(12) United States Patent
Pigg et al.

(10) Patent No.: US 12,079,238 B2
(45) Date of Patent: Sep. 3, 2024

(54) STORYTELLING VISUALIZATION OF GENEALOGY DATA IN A LARGE-SCALE DATABASE

(71) Applicant: Ancestry.com DNA, LLC, Lehi, UT (US)

(72) Inventors: Christopher Leon Pigg, Saratoga Springs, UT (US); Blake Longmore, Saratoga Springs, UT (US); James Bruce Kolste, Pleasant Grove, UT (US); Gopi Vijaybhaskar Addanki, Riverton, UT (US); James Parker Ferry, Cedar Hills, UT (US); Bryan Joseph Johnson, American Fork, UT (US); Shauri Fay Johnson, Orem, UT (US); Connie Wing Zhu Chen, San Jose, CA (US); Phillip John Wood, Salt Lake City, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 17/871,283

(22) Filed: Jul. 22, 2022

(65) Prior Publication Data
US 2023/0025175 A1 Jan. 26, 2023

Related U.S. Application Data

(60) Provisional application No. 63/224,746, filed on Jul. 22, 2021.

(51) Int. Cl.
*G06F 16/26* (2019.01)
*G06F 3/0482* (2013.01)
*G06F 3/04845* (2022.01)
*G06F 3/0485* (2022.01)

(52) U.S. Cl.
CPC ............ *G06F 16/26* (2019.01); *G06F 3/0482* (2013.01); *G06F 3/04845* (2013.01); *G06F 3/0485* (2013.01); *G06F 2203/04803* (2013.01)

(58) Field of Classification Search
CPC .... G06F 16/26; G06F 3/0482; G06F 3/04845; G06F 3/0485; G06F 2203/04803
See application file for complete search history.

(56) References Cited

U.S. PATENT DOCUMENTS

| | | | |
|---|---|---|---|
| 10,395,175 B1 * | 8/2019 | Teodorescu-Badia | ....................... G06N 5/022 |
| 10,572,831 B1 * | 2/2020 | Do | ......................... G16B 40/30 |
| 2011/0119578 A1 * | 5/2011 | Schwartz | .............. G06F 3/0485 345/173 |

(Continued)

*Primary Examiner* — Jennifer N Welch
*Assistant Examiner* — Reji Kartholy
(74) *Attorney, Agent, or Firm* — Fenwick & West LLP

(57) ABSTRACT

A storytelling interface comprising a map panel and a genealogy panel, and methods for using the same, are described. The storytelling interface facilitates dynamic and automatic scaling and relocation of the map panel based on a user's location within the genealogy panel, which facilitates a continuous scrolling operation to navigate between different sections of the genealogy panel. The storytelling interface facilitates a user receiving, viewing, and interacting with DNA and ethnic communities results determined from DNA testing, and allows a user to navigate through pertinent communities in both time and/or space.

20 Claims, 16 Drawing Sheets

(56) References Cited

U.S. PATENT DOCUMENTS

| | | | |
|---|---|---|---|
| 2012/0221977 A1* | 8/2012 | Rasmussen | G06Q 10/00 |
| | | | 715/835 |
| 2014/0359510 A1* | 12/2014 | Graf | G01C 21/3667 |
| | | | 715/771 |
| 2016/0225057 A1* | 8/2016 | Pellow | G06F 16/9537 |
| 2017/0052672 A1* | 2/2017 | Forstall | G01C 21/367 |
| 2017/0329891 A1* | 11/2017 | Macpherson | G16B 50/30 |
| 2019/0247326 A1* | 8/2019 | Ho | A61K 31/19 |

* cited by examiner

CAUSE A CLIENT DEVICE TO DISPLAY A GRAPHICAL USER INTERFACE, THE GRAPHICAL USER INTERFACE COMPRISING A GENEALOGY PANEL AND A MAP PANEL, THE GENEALOGY PANEL COMPRISING A PLURALITY OF SEGMENTS, THE PLURALITY OF SEGMENTS COMPRISING A FIRST SEGMENT DISPLAYING FIRST GENEALOGY INFORMATION RELATED TO A USER, THE MAP PANEL CONFIGURED TO DISPLAY A GEOGRAPHICAL MAP VISUALIZING INFORMATION CORRESPONDING TO THE FIRST GENEALOGY INFORMATION RELATED TO THE USER RESPONSIVE TO THE FIRST SEGMENT BEING DISPLAYED
310

RECEIVE ONE OR MORE ACTIONS OF A USER INPUT DEVICE, THE ONE OR MORE ACTIONS DIRECTED TO THE GENEALOGY PANEL CAUSING THE GENEALOGY PANEL TRANSITIONING FROM THE FIRST SEGMENT TO A SECOND SEGMENT, THE SECOND SEGMENT DISPLAYING SECOND GENEALOGY INFORMATION
320

CAUSE THE MAP PANEL OF THE GRAPHICAL USER INTERFACE TO AUTOMATICALLY ADJUST A SCALE, A LOCATION, AND/OR AN ANNOTATION OF THE GEOGRAPHICAL MAP TO VISUALIZE INFORMATION CORRESPONDING TO THE SECOND INFORMATION
330

STORYTELLING VISUALIZATION OF GENEALOGY DATA IN A LARGE-SCALE DATABASE

CROSS-REFERENCE TO RELATED APPLICATION

The present application claims the benefit of U.S. Provisional Patent Application No. 63/224,746, filed on Jul. 22, 2021, which is hereby incorporated by reference in its entirety.

FIELD

The disclosed embodiments relate to providing a storytelling interface including a dynamically and automatically adjustable map panel and an information panel for graphically illustrating complex data in a large-scale database.

BACKGROUND

A large-scale database such as a genealogy database can include billions of data records. This type of database may allow users to build family trees, research their family history, and make meaningful discoveries about the lives of their ancestors. Users may try to identify relatives with datasets in the database. However, identifying relatives in the sheer amount of data is not a trivial task. Datasets associated with different individuals may not be connected without a proper determination of how the datasets are related. Comparing a large number of datasets without a concrete strategy may also be computationally infeasible because each dataset may also include a large number of data bits. Given an individual dataset and a database with datasets that are potentially related to the individual dataset, it is often challenging to identify a dataset in the database that is associated with the individual dataset.

For example, users of genealogy sites are often overwhelmed by the volume and arrangement of information about themselves and their ancestors. In services that show location-specific information about a user, such as the locations of ethnic communities from which the user is determined to have likely descended, it is often difficult and frustrating for a user to navigate through the available information. As a result, users sometimes give up and leave the service or site before they are able to receive and interact with the information or features that would otherwise lead to a satisfying user experience.

SUMMARY

Disclosed herein relates to example embodiments that are related to a computer-implemented method. The method may include causing a client device to display a graphical user interface. The graphical user interface may include a genealogy panel and a map panel. The genealogy panel may include a plurality of segments. The plurality of segments may include a first segment displaying first genealogy information related to a user. The map panel may be configured to display a geographical map visualizing information corresponding to the first genealogy information related to the user responsive to the first segment being displayed. The method may include receiving one or more actions of a user input device. One or more actions may be directed to the genealogy panel causing the genealogy panel to transition from the first segment to a second segment. The second segment may display second genealogy information related to the user. The method may further include causing the map panel of the graphical user interface to automatically adjust a scale, a location, and/or an annotation of the geographical map to visualize information corresponding to the second information.

In some embodiments, the genealogy panel is scrollable between the plurality of segments.

In some embodiments, the genealogy panel is scrollable vertically and the map panel automatically visualizes the information corresponding to the second genealogy information responsive to a threshold portion of the second segment being scrolled into a display area of the genealogy panel.

In some embodiments, the map panel is configured to display one or more subregions corresponding to the segment of the genealogy panel that is currently displayed on the graphical user interface, e.g. within the display area.

In some embodiments, the genealogy panel includes one or more selectable options within at least one segment of the plurality of segments.

In some embodiments, the method may further include causing the map panel to highlight a subregion corresponding to a selected segment of the genealogy panel.

In some embodiments, the subregion of the map panel is a geographic boundary of at least one of the ethnic communities.

In some embodiments, the method may further include causing the map panel to display only a portion of a subregion that exceeds a predetermined confidence interval threshold.

In some embodiments, the predetermined confidence interval threshold is 75%.

In some embodiments, one of the segments in the genealogy panel includes information regarding one or more ethnic communities based on DNA results.

In some embodiments, one of the segments in the genealogy panel includes selectable options for ethnic communities to which a user is determined to belong.

In some embodiments, the genealogy panel is configured to provide a second view when a selectable option is selected, the second view providing information pertaining to the selectable option.

In some embodiments, the map panel is capable of relocating and/or adjusting a scale continuously.

In some embodiments embodiment, a non-transitory computer readable medium that is configured to store instructions is described. The instructions, when executed by one or more processors, cause the one or more processors to perform a process that includes steps described in the above computer-implemented methods or described in any embodiments of this disclosure. In some embodiments, a system may include one or more processors and a storage medium that is configured to store instructions. The instructions, when executed by one or more processors, cause the one or more processors to perform a process that includes steps described in the above computer-implemented methods or described in any embodiments of this disclosure.

BRIEF DESCRIPTION OF THE DRAWINGS

FIG. 3 is a flowchart depicting an example process for causing to display a storytelling graphical user interface, in accordance with some embodiments.

Figure 1:
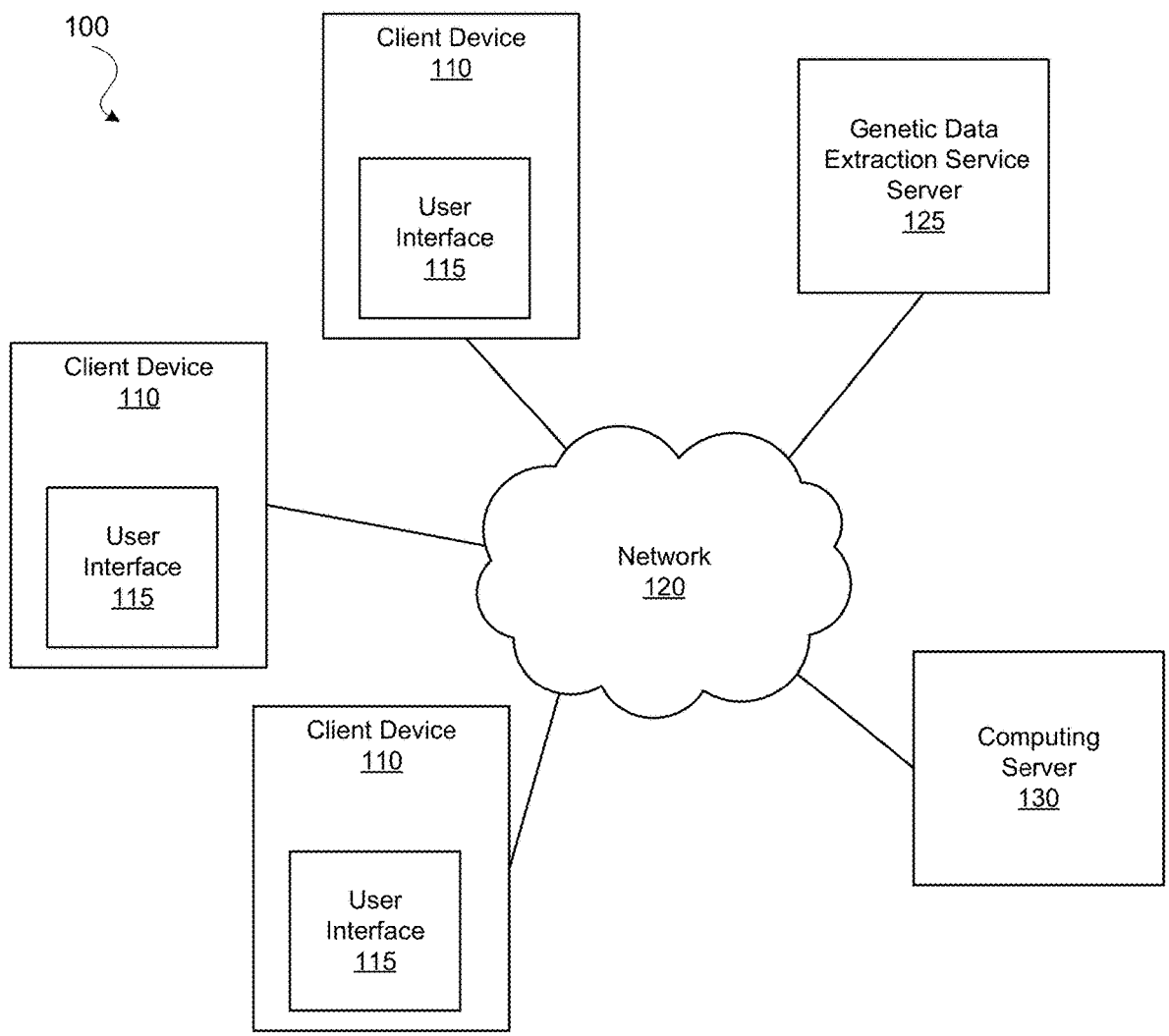
FIG. 1 illustrates a diagram of a system environment of an example computing system, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGS.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Embodiments of storytelling interfaces advantageously provide for a more engaging and more intuitive user experience without sacrificing the depth, breadth, and quality of features and information that may be displayed to a user. The storytelling interfaces may include a genealogy panel and a map panel configured to cooperate with each other based on a user's scrolling location and/or speed. The storytelling interfaces may likewise be configured to provide or display features and/or information regarding ethnicity or community, such as an ethnic heritage of a user. This may include showing historical ethnic communities that the user's DNA is determined to match.

Users who provide DNA samples may be determined to belong to or descend from a particular ethnic community, which may be determined to differ through time. For example, the DNA profile of a user may match a community of known Eastern European/Russian people, the metes and bounds of which community may be determined to vary through time, and can be displayed on a map. A user may have DNA segments corresponding to a plurality of communities, with an estimated percentage of the user's genetic signature attributed to each community of the plurality of communities: for example, 10% Eastern European/Russian, 10% Baltics, 10% England and Northwestern Europe, 10% Ireland, 10% Northern Italy, 10% Southern Italy, 10% Scotland, 10% Wales, 5% Germanic Europe, 5% Greece and Albania, 5% Malta, and 5% Sweden. Different users may have any number of different combinations and proportions.

The ethnic communities that correspond to one of the above regions, or a different region, may be displayed to a user on a map panel of a storytelling interface, with determined metes and bounds of the ethnic communities not necessarily corresponding to modern geographical boundaries. Moreover, subregions of the ethnic communities may be determined based on a percent confidence threshold. For example, only that portion of a particular region (like Russia) that exceeds a 75% confidence interval may be shown to a user in certain views of the map. In other views, the different confidence intervals are reflected in different treatment of the ethnic community as shown on a map, for instance by differently shading the different subregions.

Each region may be differentiated from the others by suitable means, such as by providing different colors to shade the different regions/community boundaries. This allows a user to observe a dynamic and aesthetically engaging map of their ethnic heritage.

Example System Environment

FIG. 1 illustrates a diagram of a system environment 100 of an example computing server 130, in accordance with an embodiment. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliance (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In one embodiment, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more subnetworks, which may include any combination of local area and/or wide area networks, using both wired and/or wireless communication systems. In one embodiment, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. In one embodiment, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In one embodiment, a set of SNPs (e.g., 300,000) that are shared between different array platforms (e.g., Illumina OmniExpress Platform and Illumina HumanHap 650Y Platform) may be obtained as the genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms and include information regarding various biomarkers of an individual. For example, in one embodiment, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In one embodiment, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual. SNPs, base pair sequence, genotype, haplotype, RNA sequences, protein sequences, phenotypes are examples of biomarkers.

The computing server 130 performs various analyses of the genetic data, genealogy data, and users' survey responses to generate results regarding the phenotypes and genealogy of users of computing server 130. Depending on the embodiments, the computing server 130 may also be referring to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees.

In one embodiment, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In one embodiment, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
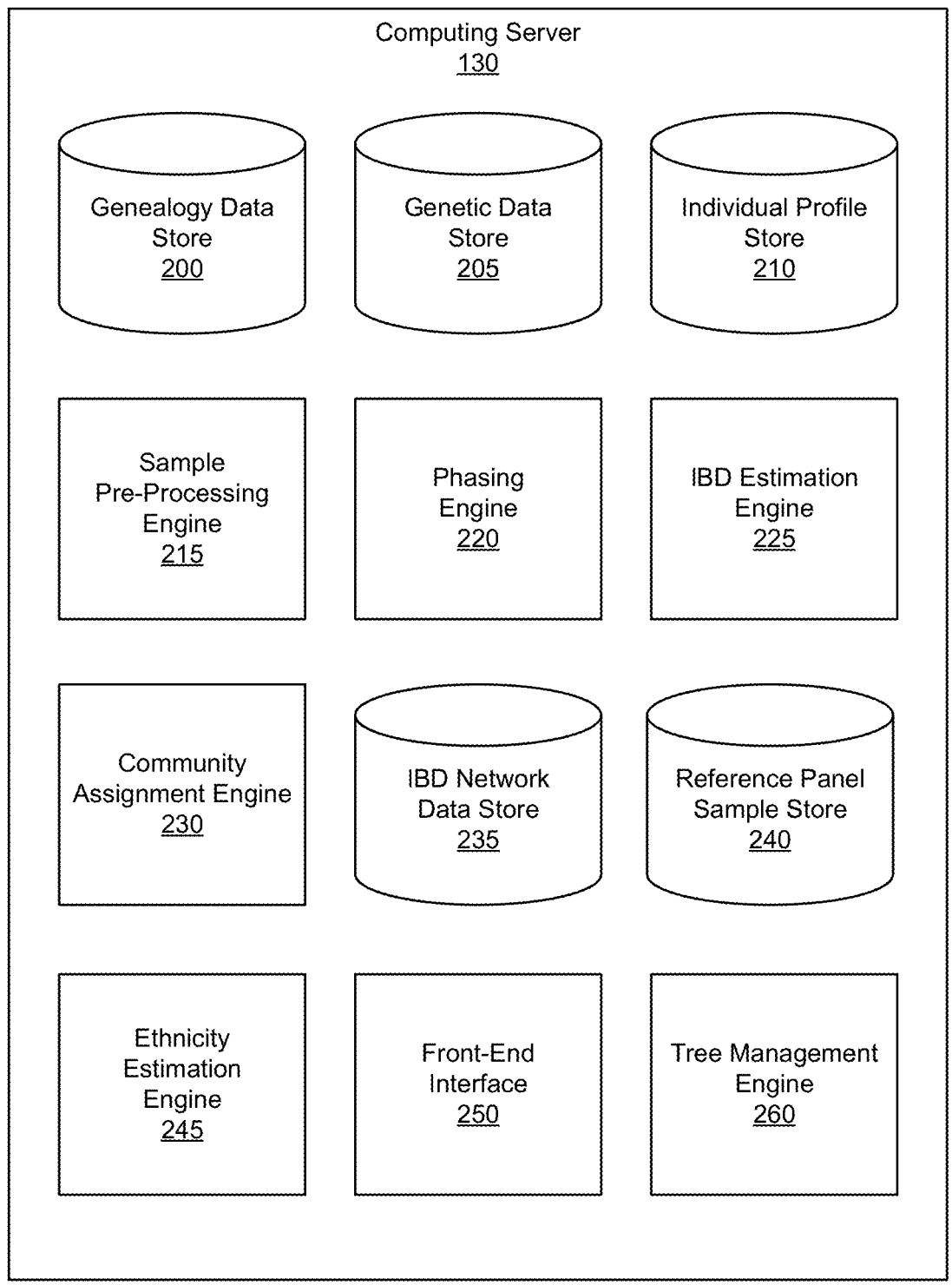
FIG. 2 is a block diagram of an architecture of an example computing system, in accordance with some embodiments.

FIG. 2 is a block diagram of an architecture of an example computing server 130, in accordance with an embodiment. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, and a front-end interface 250. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogy data, and survey response data. The computing server 130 processes the genetic data of users to identify shared identity-by-descent (IBD) segments between individuals. The genealogy data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to the basic information of the user (e.g., name, date of birth, birthplace, etc.) and later on more advanced questions that may be useful for obtaining additional genealogy data. The computing server 130 may also include survey questions regarding various traits of the users such as the users' phenotypes, characteristics, preferences, habits, lifestyle, environment, etc.

Genealogy data may be stored in the genealogy data store 200 and may include various types of data that are related to tracing family relatives of users. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, offspring in some cases. Genealogy data may also include connections and relationships among users of the computing server 130. The information related to the connections among a user and her relatives that may be associated with a family tree may also be referred to as pedigree data or family tree data.

In addition to user-input data, genealogy data may also take other forms that are obtained from various sources such as public records and third-party data collectors. For example, genealogical records from public sources include birth records, marriage records, death records, census records, court records, probate records, adoption records, obituary records, etc. Likewise, genealogy data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogy data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data of the whole or portions of an individual's genome. The genetic data store 205 may store a pointer to a location associated with the genealogy data store 200 associated with the individual. A genetic dataset may take different forms. In one embodiment, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP loci (e.g., allele sites) filtered from the sequencing results. A SNP locus that is single base pair long may also be referred to a SNP site. A SNP locus may be associated with a unique identifier. The genetic dataset may be in a form of diploid data that includes a sequencing of genotypes, such as genotypes at the target SNP loci, or the whole base pair sequence that includes genotypes at known SNP loci and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual.

In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogy database. A unique individual identifier may a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointer associating genetic datasets such as genotype and phased haplotype data of the individual that are saved in the genetic data store 205. The metadata about the individual may also individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In one embodiment, the user profile data may also include one or more photos of the users and photos of relatives (e.g., ancestors) of the users that are uploaded by the users. A user may authorize the computing server 130 to analyze one or more photos to extract information, such as the user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's diseases, diabetes, cancer, and obesity. The computing server 130 may obtain data of a user's disease-related phenotypes from survey questions of the health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 130 also may present various survey questions related to the environmental factors of users. In this context, an environmental factor may be a factor that is not directly connected to the genetics of the users. Environmental factors may include users' preferences, habits, and lifestyles. For example, a survey regarding users' preferences may include questions related to things and activities that users like or dislike, such as types of music a user enjoys, dancing preference, party-going preference, certain sports that a user plays, video games preferences, etc. Other questions may be related to the users' diet preference such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has a smartphone or doesn't, has a car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogy data store 200 and genetic data store 205.

The user profile data, photos of users, survey response data, the genetic data, and the genealogy data may subject to the privacy and authorization setting from the users to specify any data related to the users can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access of the data and may change the setting as wish. The privacy settings also may allow a user to specify (e.g., by opting out, by not opting in) whether the computing server 130 may receive, collect, log, or store particular data associated with the user for any purpose. A user may restrict her data at various levels. For example, on one level, the data may not be accessed by the computing server 130 for purposes other than displaying the data in the user's own profile. On another level, the user may authorize anonymization of her data and participate in studies and researches conducted by the computing server 130 such as a large-scale genetic study. On yet another level, the user may turn some portions of her genealogy data public to allow the user to be discovered by other users (e.g., potential relatives) and be connected in one or more family trees. Access or sharing of any information or data in the computing server 130 may also be subject to one or more similar privacy policies. A user's data and content objects in the computing server 130 may also be associated with different levels of restriction. The computing server 130 may also provide various notification features to inform and remind users of their privacy and access settings.

For example, when privacy settings for a data entry allow a particular user or other entities to access the data, the data may be described as being "visible," "public," or other suitable labels, contrary to a "private" label.

In some cases, the computing server 130 may have a heightened privacy protection on certain types of data and data related to certain vulnerable groups. In some cases, the heightened privacy settings may strictly prohibit the use, analysis, sharing of data related to a certain vulnerable group. In other cases, the heightened privacy settings may specify that data subject to those settings require prior approval for access, publication, or other use. In some cases, the computing server 130 may provide the heightened privacy as a default setting for certain types of data, such as genetic data or any data that the user marks as sensitive. The user may opt in for sharing of those data or change the default privacy settings. In other cases, the heightened privacy settings may apply across the board for all data of certain groups of users. For example, if the computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

The sample pre-processing engine 215 receives and pre-processes data received from various sources to change the data into a format used by the computing server 130. For genealogy data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. The human genome mutation rate is estimated to be $1.1*10^{-8}$ per site per generation. This may lead to a variant of approximately every 300 base pairs. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. In one embodiment, the SNPs may be autosomal SNPs. In one embodiment, 700,000 SNPs may be identified in an individual's data and may be stored in genetic data store 205. Alternatively, in one embodiment, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No. 10,679,729, entitled "Haplotype Phasing Models," granted on Jun. 9, 2020, describes example embodiments of haplotype phasing.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogy data store 200. U.S. Pat. No. 10,114,922, entitled "Identifying Ancestral Relationships Using a Continuous stream of Input," granted on Oct. 30, 2018, and U.S. Pat. No. 10,720,229, entitled "Reducing Error in Predicted Genetic Relationships," granted on Jul. 21, 2020, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in one embodiment, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. Pat. No. 10,223,498, entitled "Discovering Population Structure from Patterns of Identity-By-Descent," granted on Mar. 5, 2019, describes example embodiments of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, in determining the ethnic composition of an individual, and in determining the accuracy in any genetic data analysis, such as by computing a posterior probability of a classification result from a classifier.

A reference panel sample may be identified in different ways. In one embodiment, an unsupervised approach in community detection may apply the clustering algorithm recursively for each identified cluster until the sub-clusters contain a number of nodes that are smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, other quality control. Principal component analysis may be used to creates clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In one embodiment, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node groups. Each node group, representing a window, includes a plurality of nodes.

The nodes representing different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverses the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. Pat. No. 10,558,930, entitled "Local Genetic Ethnicity Determination System," granted on Feb. 11, 2020, describes example embodiments of ethnicity estimation.

The front-end interface 250 displays various results determined by the computing server 130. The results and data may include the IBD affinity between a user and another individual, the community assignment of the user, the ethnicity estimation of the user, phenotype prediction and evaluation, genealogy data search, family tree and pedigree, relative profile and other information. The front-end interface 250 may allow users to manage their profile and data trees (e.g., family trees). The users may view various public family trees stored in the computing server 130 and search for individuals and their genealogy data via the front-end interface 250. The front-end interface 250 may also be a storytelling interface that displays various genealogy information. The computing server 130 may suggest or allow the user to manually review and select potentially related individuals (e.g., relatives, ancestors, close family members) to add to the user's data tree. The front-end interface 250 may be a graphical user interface (GUI) that displays various information and graphical elements. The front-end interface 250 may take different forms. In one case, the front-end interface 250 may be a software application that can be displayed on an electronic device such as a computer or a smartphone. The software application may be developed by the entity controlling the computing server 130 and be downloaded and installed at the client device 110. In another case, the front-end interface 250 may take the form of a webpage interface of the computing server 130 that allows users to access their family tree and genetic analysis results through web browsers. In yet another case, the front-end interface 250 may provide an application program interface (API). Various examples of the front-end interface 250 in the form of GUI are shown in FIG. 4A through FIG. 7C.

The tree management engine 260 performs computations and other processes related to users' management of their data trees such as family trees. The tree management engine 260 may allow a user to build a data tree from scratch or to link the user to existing data trees. In some embodiments, the tree management engine 260 may suggest a connection between a target individual and a family tree that exists in the family tree database by identifying potential family trees for the target individual and identifying one or more most probable positions in a potential family tree. A user (target individual) may wish to identify family trees to which he or she may potentially belong. Linking a user to a family tree or building a family may be performed automatically, manually, or using techniques with a combination of both. In an embodiment of an automatic tree matching, the tree management engine 260 may receive a genetic dataset from the target individual as input and search related individuals that are IBD-related to the target individual. The tree management engine 260 may identify common ancestors. Each common ancestor may be a common to the target individual and one of the related individuals. The tree management engine 260 may in turn output potential family trees to which the target individual may belong by retrieving family trees that include a common ancestor and an individual who is IBD-related to the target individual. The tree management engine 260 may further identify one or more probable positions in one of the potential family trees based on information associated with matched genetic data between the target individual and DNA test takers in the potential family trees through one or more machine learning models or other heuristic algorithms. For example, the tree management engine 260 may try putting the target individual in various possible location in the family tree and determine the highest probability position(s) based on the genetic datasets of the target individual and other DNA test takes in the family tree and based on genealogy data available to the tree management engine 260. The tree management engine 260 may provide one or more family trees from which the target individual may select. For a suggested family tree, the tree management engine 260 may also provide information on how the target individual is related to other individuals in the tree. In a manual tree building, a user may browse through public family trees and public individual entries in the genealogy data store 200 and individual profile store 210 to look for potential relatives that can be added to the user's family tree. The tree management engine 260 may automatically search, rank, and suggest individuals for the user conduct manual review as the user makes progress in the front-end interface 250 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Patent Publication Application No., entitled "Linking Individual Datasets to a Database," US2021/0216556, published on Jul. 15, 2021, describes example embodiments of how an individual may be linked to existing family trees.

Example Process for Displaying Storytelling GUI

FIG. 3 is a flowchart depicting an example process 300 for displaying a storytelling graphical user interface, in accordance with some embodiments. The process 300 may be performed by a computing device, such as the computing server 130. The process 300 may be embodied as a software algorithm that may be stored as computer instructions that are executable by one or more processors. The instructions, when executed by the processors, cause the processors to perform various steps in the process 300. One or more steps in the process 300 may be skipped, added, or changed in various embodiments.

The computing server 130 may cause 310 a client device 110 to display a graphical user interface. The front-end interface 250 may be an example of the graphical user interface. Various examples of the graphical user interface are shown in FIG. 4A through FIG. 7C. The graphical user interface may include a genealogy panel and a map panel. A panel is an identifiable region in the graphical user interface. Panels may take different sizes, shapes and forms, whether they are rectangular or not, fixed-sized or not, symmetrical or not, regular or irregular. Also, the panels do not need to be displayed side by side or have any particular arrangement. In some embodiments, portions of the panels can overlap each other.

For example, in some cases, in response to one or more actions by a user, a panel may temporarily increase its size and may become enlarged or even full screen. In some embodiments, a user may also select the relative sizes and shapes among the panels. Although two example panels, the map panel and the genealogy panel, are primarily discussed and shown in various examples in subsequent figures, the graphical user interface may also include additional or different panels. For example, in some embodiments, the graphical user interface may also include a user profile panel, a search panel, and a family tree panel. The automatic interactions and relationships between the map panel and the genealogy panel that are described in further detail below may also be applied to the interactions between any other panels without the loss of generality.

In some embodiments, a genealogy panel may take the form of a rectangular board that is at least partially used to display genealogy information and may additionally include interactive elements or control elements for a user to navigate through a large-scale genealogy database. The genealogy information may be tailored to the user who is using the graphical user interface. In some embodiments, genealogy information may include any information of relatives related to a target individual. Genealogy information may include information derived from various genealogy sources and information derived from DNA data. For example, genealogy information may include information determined by various engines in FIG. 2, including data stored in the genealogy data store 200, the genetic data store 205, and the individual profile store 210 and results determined by the sample pre-processing engine 215, the phasing engine 220, the IBD estimation engine 225, the community assignment engine 230, the IBD network data store 235, the ethnicity estimation engine 245, and the tree management engine 260. Genealogy information is not merely limited to family data, but could include data and information related to individuals related to the user, which may also be referred to as a target individual. Related individuals may include family members, relatives, distant relatives, people who are normally not considered relatives but are related to the target individual based on the DNA data, such as those who shared IBD segments with the target individual, and people that belong to the same ethnicity as the target individual.

In some embodiments, a genealogy panel may include multiple segments. A segment may be an identifiable region of the genealogy panel. In various embodiments, the segments in the genealogy panel may be arranged and presented in various forms, linear or branched, vertically or horizontally, continuous or discrete, sequentially or not. For example, in some embodiments, the segments may be arranged vertically and continuously similar to a feed. The genealogy panel may be associated with a display area that may vary depending on the screen resolution of the client device 110 that displays the graphical user interface. The segments arranged in the feed may in total occupy more space than the display area so that only one or a few segments in the genealogy panel are initially displayed or displayed at any given time. A user may select different segments by navigating, e.g., scrolling, through the collection of segments. Alternative to or in addition to a segment feed that is arranged vertically, the multiple segments may be arranged page by page, such as arranged horizontally as pages or sequentially, where a user may switch pages by clicking on a mouse or tabbing on the screen. Some of the segments may also be arranged discretely and in a branch. For example, one of the segments may include control elements that allow users to select one of two alternative segments and the two alternative segments are only displayed after the user affirmatively selects one of them. Other suitable ways of arranging the segments are also possible, such as arranging segments in tile form, stacking, or randomly. FIG. 4A through FIG. 7C shows various examples of segments in different screen resolutions, such as in a client device that is a computer and a client device that is a mobile phone.

The multiple segments may include various segments that include different information and functionalities. For example, a first segment may display first genealogy information related to a user, such as a target individual, which may be the person who submitted a sample for a DNA test and/or has built one or more family trees with the computing server 130. A second segment may display second genealogy information related to the user. While "first," "second," "third," etc. may be used to describe the segments, the use of those terms does not imply any sequence, order, or continuity of those segments. For example, the second segment may be a preceding segment than the first segment and there can be one or more intermediate segments between the first and the second segments. Also, while the genealogy panel is referred to as such, not every segment in the genealogy panel may contain genealogy information or only genealogy information. For example, in FIG. 6C, one or more segments may be a functional segment that includes a control element to allow a user to share a DNA story. The genealogy information among the segments may be logically related to each other. For example, one segment may provide information regarding the genetic composition of a target individual in terms of ancestral regions (e.g., FIG. 4A), and an immediately subsequent segment may provide information regarding the detail of one of the ancestral regions (e.g., FIG. 4B). Other arrangements and relationships among the segments are also possible.

The map panel may display a geographical map visualizing information corresponding to the genealogy information in the segment that is currently displayed in the genealogy panel. For example, in response to the first segment being displayed and the first segment including the first genealogy information regarding a region, the map panel automatically displays the geographical map that focuses on the region. The geographical map may also include or illustrate shading, highlight, boundary, contracts, and other annotations to further emphasize or illustrate the genealogy information that is currently presented in the segment of the genealogy panel.

The map panel may be configured to automatedly zoom and/or center the geographic map so as to focus a user's attention on the region. For example, where the region is an ethnic group or community pertaining to Mongolia, the map panel zooms so that the margins surrounding the region of interest (e.g. boundaries drawn proximate Mongolia) are minimized, while incorporating the entirety or substantial entirety of the region of interest. Further, a center, e.g. centroid, of the region of interest may be aligned to a center of the map panel.

The computing server 130 may receive 320 one or more actions of a user input device. The one or more actions may be directed to the genealogy panel, which causes the genealogy panel to transition from the first segment to a second segment. The second segment may contain or display different, e.g. second, information compared to the first segment and the corresponding first information. A user input device may be one of the components of a client device 110. Examples of a user input device may include the graphics display unit 810, the alphanumeric input device 812, and the cursor control device 814 described in FIG. 8. The type of user input device used may depend on the client device 110. For example, if the client device 110 is a computer, the user input device may be a mouse, a keyboard, or a touch pad. If the client device 110 is a tablet or a smartphone, the user input device may be a touch screen display.

In various embodiments and situations, the actions directed to the genealogy panel may be different. The actions may be scrolling using a mouse or an equivalent action when a user is using a touch screen display or a touch pad, such as sliding using a particular number of fingers or sliding at a particular location and/or direction of the touch pad. Other actions, such as keyboard actions, mousing clicking in a control element of the genealogy panel, hovering, tapping, spinning, etc. are also possible. The actions may be continuous or discrete. For example, in one case, the segments are arranged vertically and continuously, and the action may be a continuous scrolling or continuous sliding until the first segment is transitioned to the second segment. In some embodiments, different actions may result in different types of transitions. For example, the graphical user interface may react differently in response to hovering and a click.

The transition from one segment to another segment may also depend on the type of user actions and the arrangement of the segments. In some embodiments, the segments are arranged continuously like a feed (whether vertically or horizontally), and the transition therebetween may be continuous as the first segment is partially moved out of the display area of the genealogy panel and the second segment is partially moved into the display area. In this type of arrangement, the transition point may be defined in any suitable manner, such as by a predefined threshold. For example, each segment may have a reference point (e.g., the vertical midpoint, the highest point, the N % vertical point) and the display area may also have a reference point (e.g., top of the display area, the center of the display area, N % height of the display area). A segment may be regarded as being transitioned and displayed at the genealogy panel when the segment reference point passes the display area reference point. For example, if the segments are arranged vertically and the user is scrolling down from the first segment to the second segment, the genealogy panel may be considered as having transitioned to the second segment when the second segment's vertical midpoint is above the display area center. Other ways to define the transition between segments are also possible. For example, when a majority of a segment is displayed, the segment may be considered as being displayed. In some embodiments, the entire collection of segments or one or more segments may not be arranged continuously. For example, one segment may only be displayed as a new page. In response to a user clicking a control element, the genealogy panel may transition to that segment by loading a new page. In some embodiments, the display area may also be capable of displaying more than one segment. Rules may be defined to select one of the displayed segments for the map panel to display corresponding geographical information.

The computing server 130 may cause 330 the map panel of the graphical user interface to automatically adjust a scale and/or a location and/or an annotation of the geographical map to visualize information corresponding to the second information. In some embodiments, the automatic nature may allow the user to perform actions on the genealogy panel and the map panel automatically adjusts itself to provide the information corresponding to the genealogy panel. For example, the user may not need to direct an action to the map panel. The change of the map panel may include zooming in and zooming out of a world map, jumping to another location, and annotating the map differently. In some embodiments, since the user may not need to control the map panel, the transition in the map panel may be seamless. For example, in some embodiments, the segments in the genealogy panel may be arranged continuously similar to a feed, as the user scroll through different segments, the map panel may automatically zoom in and out of a map to display various information corresponding to the genealogy information currently displayed at the genealogy panel. The transition may also correspond to the user's scrolling speed. For example, a fast downward scrolling in the genealogy panel may correspond to fast zooming in on the map in the map panel.

Other automatic transitions are also possible. For example, a user may click on a control element of the genealogy panel and the genealogy panel loads a new page, and the map panel may automatically jump to another location corresponding to the new page. The seamless transition of the map panel may also include a locality of the map panel. For example, a user may highlight (e.g., tap, highlight, or otherwise select) a location name, an individual name, or another piece of information in the genealogy panel, and the map panel may automatically generate an annotation or highlight on the map based the user action.

While the map panel is described as automatic in various examples, in some embodiments the map panel may also include manual control elements. For example, after the map panel automatically zooms in in response to a transition to a new segment in the genealogy panel, the user may manually perform various actions on the map, including adjusting the locations and scales and adding manual annotations. In some embodiments, use reactions in the map panel may effect changes in the genealogy panel, e.g. by automatically scrolling to a segment of the genealogy panel based on a user clicking or otherwise selecting a corresponding location, genetic community, or other feature in the map panel.

FIG. 4A through FIG. 7C are various graphical illustrations of example graphical user interfaces. The transitions in various stages illustrated in those figures are examples of the transitions described in FIG. 3.

Example Storytelling GUI

Embodiments of storytelling interfaces advantageously provide for a more-engaging and more-intuitive user experience without sacrificing the depth, breadth, and quality of features and information that may be displayed to a user. The storytelling interfaces may include a genealogy panel and a map panel configured to cooperate with each other based on a user's scrolling location and/or speed. The storytelling interfaces may likewise be configured to provide or display features and/or information regarding ethnicity, such as an ethnic heritage of a user. This may include showing historical ethnic communities that the user's DNA is determined to match. In various embodiments, ethnic communities may include people's communities and/or ethnicities.

Users who provide DNA samples may be determined to belong to or descend from a particular ethnic community, which may be determined to differ through time. For example, the DNA profile of a user may match a community of known Eastern European/Russian people, the metes and bounds of which community may be determined to vary through time, and can be displayed on a map. A user may have DNA segments corresponding to a plurality of communities, with an estimated percentage of the user's genetic signature attributed to each community of the plurality of communities: for example, 10% Eastern European/Russian, 10% Baltics, 10% England and Northwestern Europe, 10% Ireland, 10% Northern Italy, 10% Southern Italy, 10% Scotland, 10% Wales, 5% Germanic Europe, 5% Greece and Albania, 5% Malta, and 5% Sweden. Different users may have any number of different combinations and proportions.

The ethnic communities that correspond to one of the above regions, or a different region, may be displayed to a user on a map panel of a storytelling interface, with determined metes and bounds of the ethnic communities not necessarily corresponding to modern geographical boundaries. Moreover, subregions of the ethnic communities may be determined based on a percent confidence threshold. For example, only that portion of a particular region (like Russia) that exceed a 75% confidence interval may be shown to a user in certain views of the map. In other views, the different confidence intervals are reflected in different treatment of the ethnic community as shown on a map, for instance by differently shading the different subregions.

Each region may be differentiated from the others by suitable means, such as by providing different colors to shade the different regions/community boundaries. This allows a user to observe a dynamic and aesthetically engaging map of their ethnic heritage.

Figure 4A:
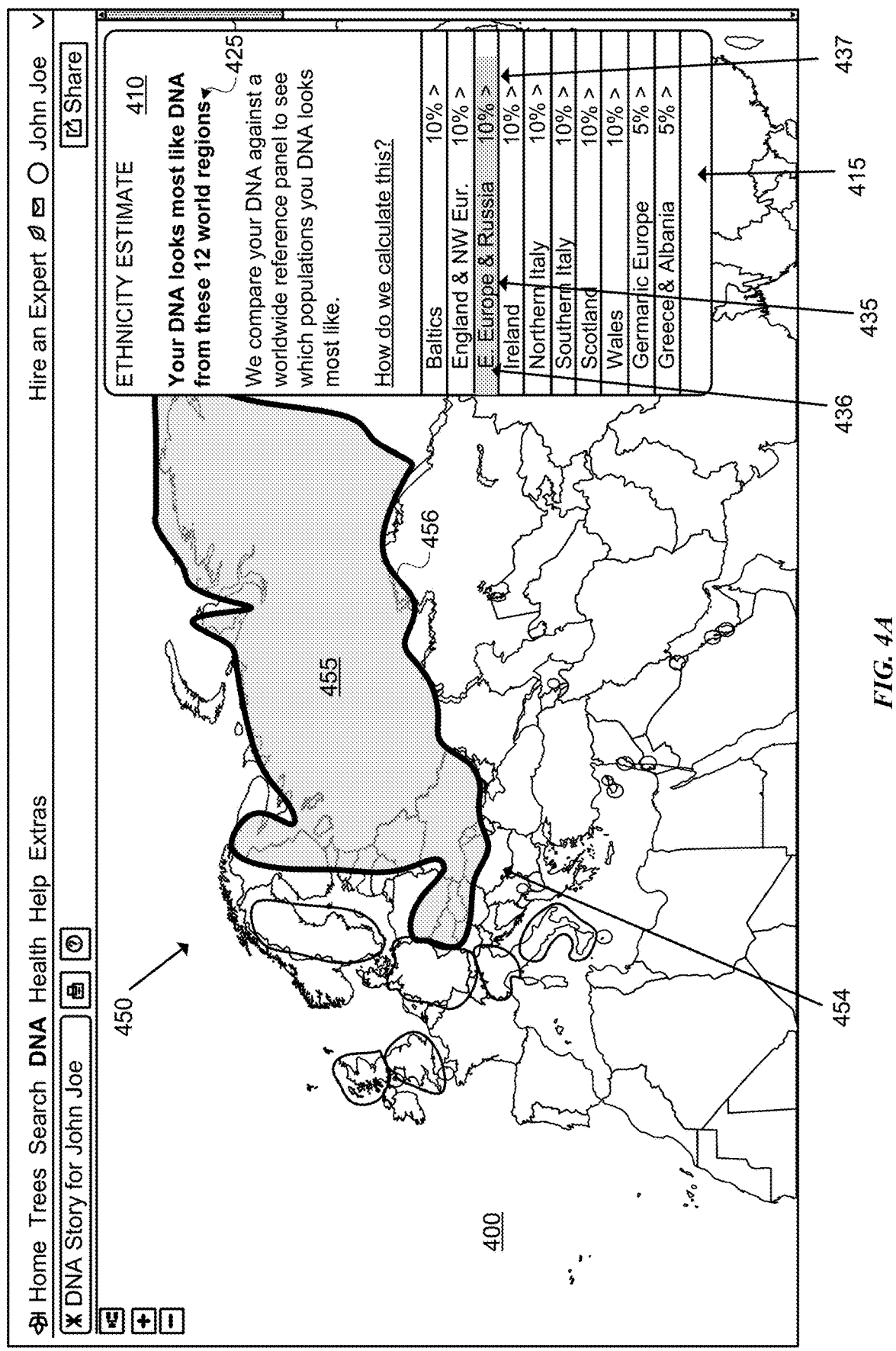
FIG. 4A shows a first view of a first mode of a storytelling interface, in accordance with some embodiments.

Turning to FIG. 4A, the first view of a first mode of a storytelling interface is shown. The first view includes a map panel 400 and a genealogy panel 410, which are configured to cooperate with each other. In some embodiments, a user may scroll through the genealogy panel 410 in a continuous fashion, allowing the user to observe features of the storytelling interface without having to understand potentially a complex organization or arrangement of features of the site. As the user scrolls up or down through the genealogy panel 410, the map panel 400 automatically updates according to the location or segment of the genealogy panel 410 that is currently being displayed.

The map panel 400 shows at least a portion of a geographical map (e.g., a world map 450) and overlays thereon regions 454 corresponding to the boundaries of ethnic communities. In the depicted embodiment, each community from which a user is determined to be descended (based on their DNA results) is overlaid on the world map 450. The scale of the world map 450 is adjusted by the storytelling interface such that, in a first mode, all regions 454 pertinent to the user based on their DNA are simultaneously visible. This is merely exemplary and any suitable scale or selection of regions may be used.

In FIG. 4A, the user may be presented with a first segment 415 of the genealogy panel 410 showing first genealogy information 425 and options 435, which may include control elements. For example, each row in options 435 may be selectable. The first genealogy information 425 provides information regarding the user's DNA test results and matches therefrom, such as regions, communities, ethnic groups, individuals, or otherwise to which the user relates or belongs. The options 435 provide community options. The options 435 include for example a percentage 437 of the user's genome that is attributable to said community and an icon or indicium 436 matching the option 435 to a color of a corresponding region 454 in the map panel 400. The genealogy panel 410 allows a user to hover over the options 435 to see a highlighted version of one of the communities from which the user is descended. In FIG. 4A, when hovering over Eastern Europe and Russia (as illustrated by a shared area) that corresponding region 455 on the map panel 400 is highlighted and made more prominent, either in brightness or size. This is merely exemplary and other permutations are contemplated.

A border 456 of a selected or hovered-over option 435 may likewise be differentiated from borders of other communities, with the border 456 having a larger, more distinctive, interactive, or moving pattern that engages a user. In some embodiments, the border 456 and the shape of the region 454 itself is selected based on a determined confidence level threshold, such that only those parts of a geographic region that are determined above a suitable threshold, such as 75% confidence, are shown in the first view of the first mode in FIG. 4A. Other permutations are possible and contemplated.

Figure 4B:
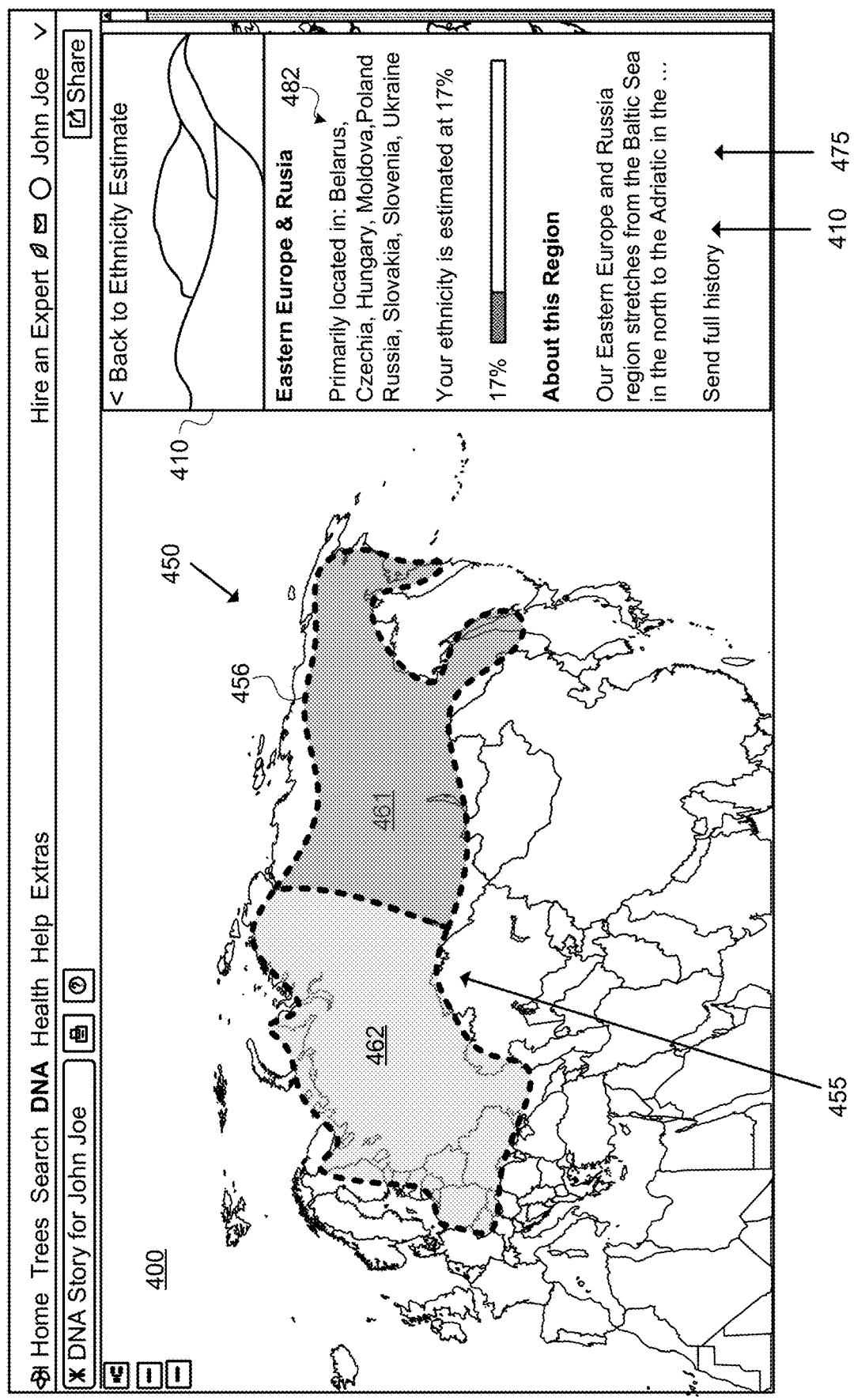
FIG. 4B shows a second view of the first mode of the storytelling interface, in accordance with some embodiments.

Turning to FIG. 4B, a second view of the first mode of FIG. 4A is shown. The second view is displayed to a user upon clicking on one of the options 435 in FIG. 4A. Whereas hovering over the option 435 in FIG. 4A highlights or accentuates the corresponding region on the map panel 400, clicking on the option 435 navigates the user to a second segment 475 of the genealogy panel 410 as shown in FIG. 4B, with different and more-specific information, such as the second genealogy information 482, shown thereon. The segment 475 is itself scrollable and provides drilled-down information on the selected ethnic community, for example, information about the culture or history of that region.

The segment 475 also includes a scale showing what percentage of a user's genome corresponds to that particular option and images or other geographic information about the genetic community, ethnicity, or otherwise. The map panel 400 automatically scales and moves upon the option 435 being selected so as to focus on and show only that particular region. As seen in FIG. 4B, the region includes a larger area than that shown in FIG. 4A, as subregions falling below a confidence interval threshold, for example, confidence areas below 75%, can be shown in contrast to FIG. 4A where the lower-confidence regions are omitted. Such subregions can be highlighted by providing distinctive shading 461 relative to a shading 462 of the higher-confidence subregions. While expanding the region upon selecting the option 435 so as to display the segment 475 is depicted, other permutations are possible.

Figure 4C:
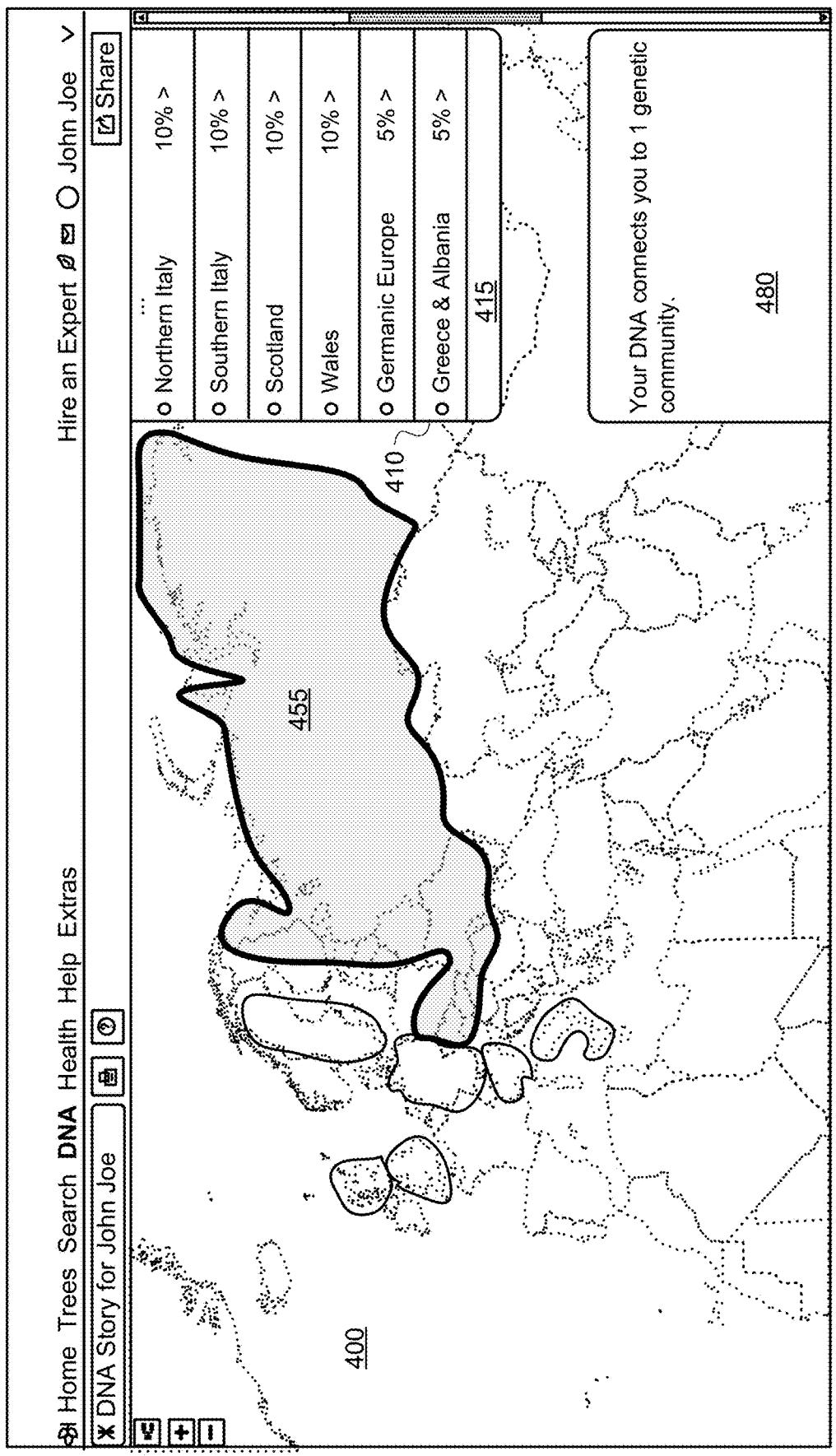
FIG. 4C shows a third view of the first mode of the storytelling interface, in accordance with some embodiments.

Turning now to FIG. 4C, a third view of the first mode of the storytelling interface is shown and described. The map panel 400 may return to the original view shown in FIG. 4A upon a user returning from the region-specific segment 475

(shown in FIG. 4B) of the storytelling interface to the main view. The genealogy panel 410 is scrollable, providing a user an intuitive way to progress through the available information. A third segment 480 of the genealogy panel 410 becomes visible as the user scrolls down from the first segment 415. Upon a certain percentage or other suitable metrics of the third segment 480 of the genealogy panel 410 becoming visible as a result of scrolling, the map panel 400 automatically adjusts to a region and scale corresponding to the third segment 480.

Figure 5A:
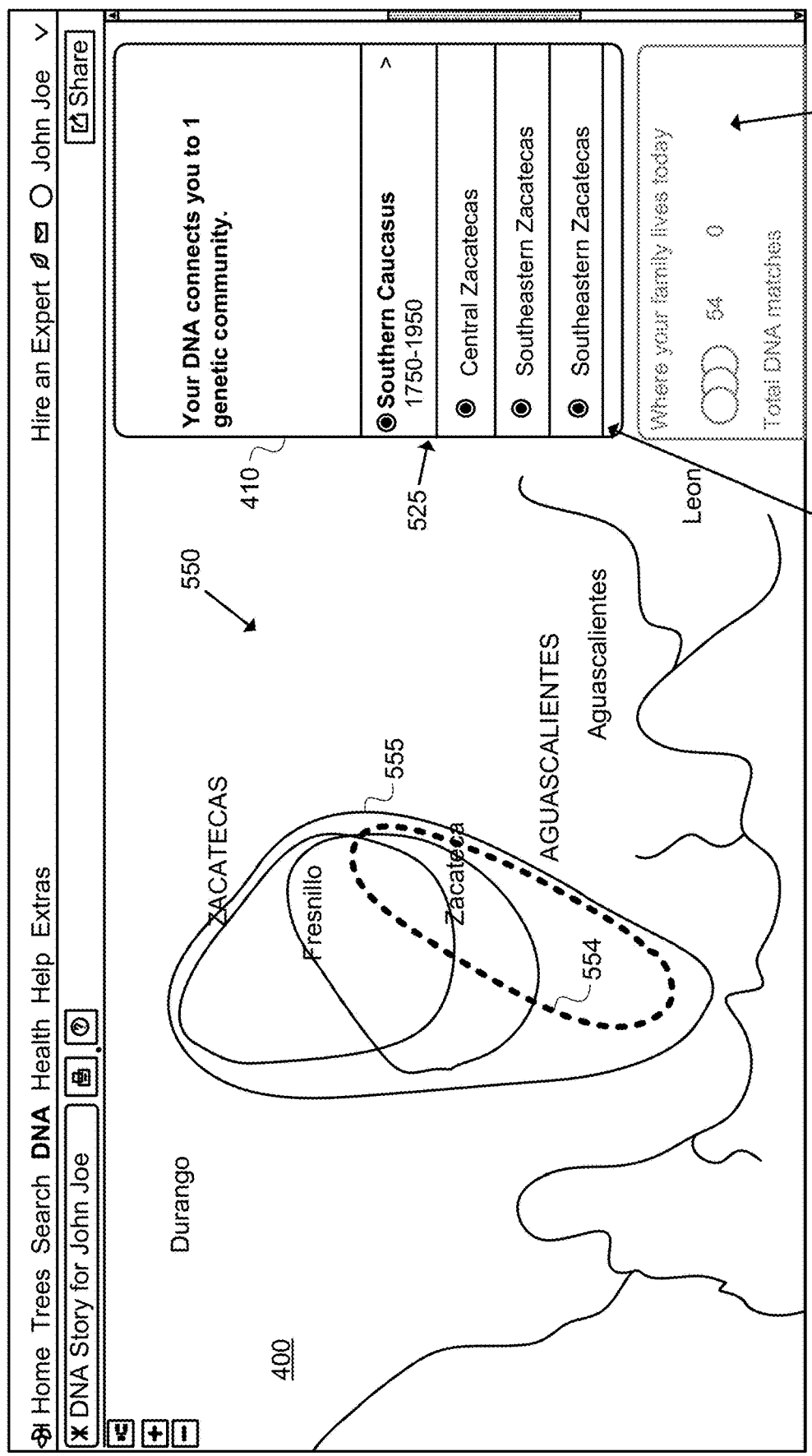
FIG. 5A shows a first view of a second mode of the storytelling interface, in accordance with some embodiments.

Turning now to FIG. 5A, a first view of the second mode of the storytelling interface is shown and described. A map panel 400 corresponds to the genealogy panel 410, where a first segment 515 corresponding to the features and information of the map panel 400 is shown. As before, a second segment 517 becomes visible as a user scrolls, but does not automatically adjust the map until a certain percentage of the second segment 517 is visible (e.g. above 90% of the second segment 517 is visible) and/or a certain percentage of the first segment 515 is no longer visible (e.g. less than 75% of the second mode). This advantageously guides a user to continue scrolling after digesting the information in the map panel 400 and the genealogy panel first segment 515. For further ease of navigation, the first segment 515 may be highlighted when the map panel 400 corresponding thereto is displayed, while the second segment 517 may be faded or otherwise distinguished. This further helps a user to understand what information is currently being displayed and where they may further navigate to after viewing the information on the map panel 400 (e.g. they can see whether there is more information to see when scrolling up or down).

The map panel 400 shows a portion 550 of a world map, the portion 550 being selected based on the geographical bounds of the regions 555 shown in or corresponding to the first segment 515. In the embodiment shown in FIG. 5A, the portion 550 is narrowed, e.g. zoomed in, from the portion of the world map shown in FIG. 4A to focus on a genetic community such as the Southern Zacatecas community in Mexico. The first segment 515 provides options 525 corresponding to particular subregions 554 within a community. The subregions 554 are displayed on the map panel 400. As above, the user may hover over one of the options 525 and the corresponding subregion 554 will be highlighted or otherwise differentiated from the impertinent subregions 554.

Figure 5B:
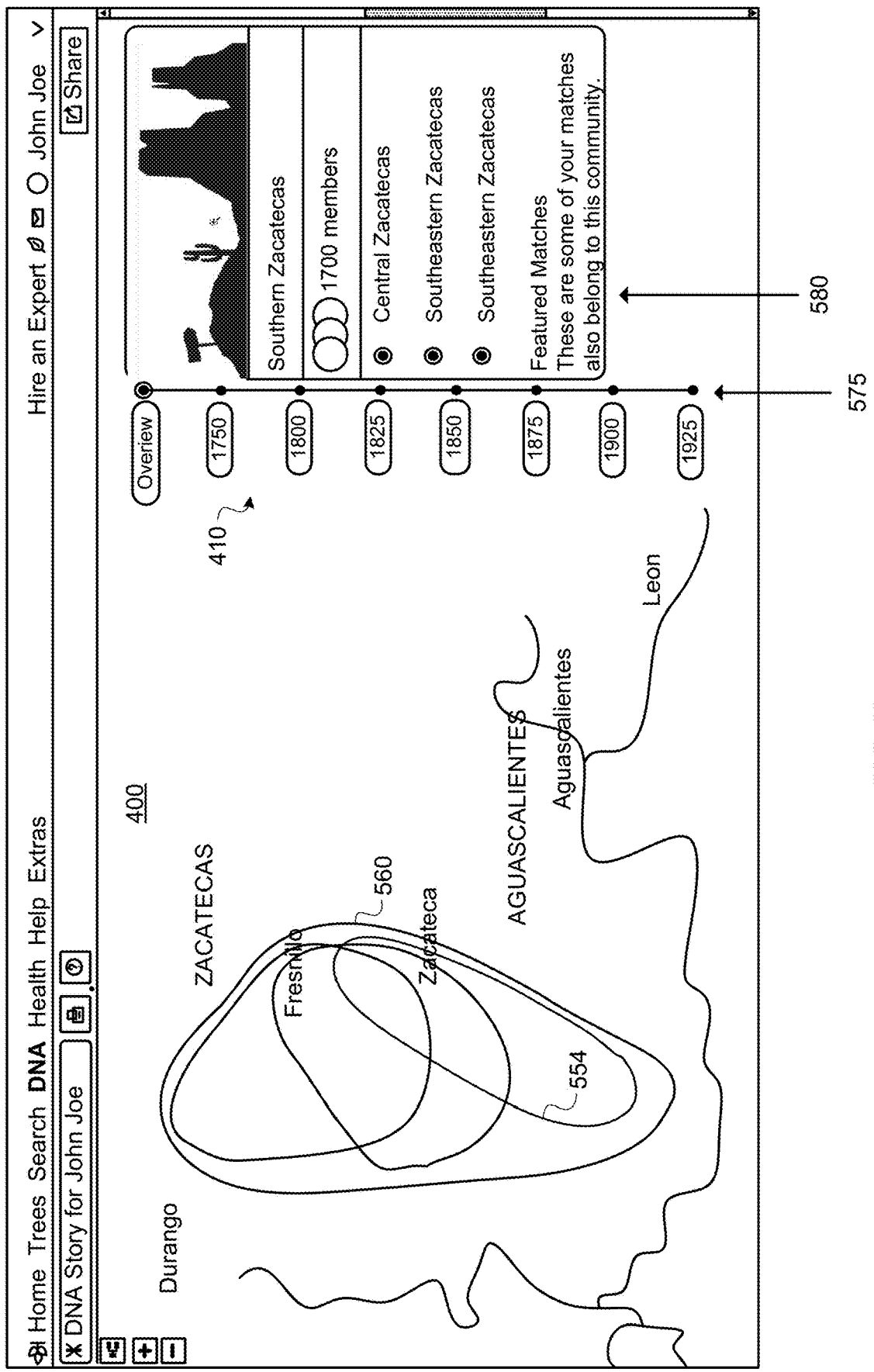
FIG. 5B shows a second view of the second mode of the storytelling interface, in accordance with some embodiments.

Referring to FIG. 5B, instead of hovering, the user can click on one of the options 525 and be navigated to a separate genealogy segment 580, where facts, histories, pictures, members of the site or DNA testing service who pertain to that community, links, and other information may be displayed. The genealogy panel 410 may provide a timeline feature 575 that allows a user to navigate both the genealogy panel 410 and the corresponding features displayed on the map panel 400 with ease, as hovering over or clicking on any of the discrete times (e.g. years, such as 1750, 1800, 1850, etc.) changes the map panel 400 to show a granular breakdown 560 of the ethnic/genetic community pertaining to that timeframe and/or automatically scrolls the genealogy panel 410 to a corresponding portion of the genealogy panel, e.g. a snippet regarding the selected time.

Figure 5C:
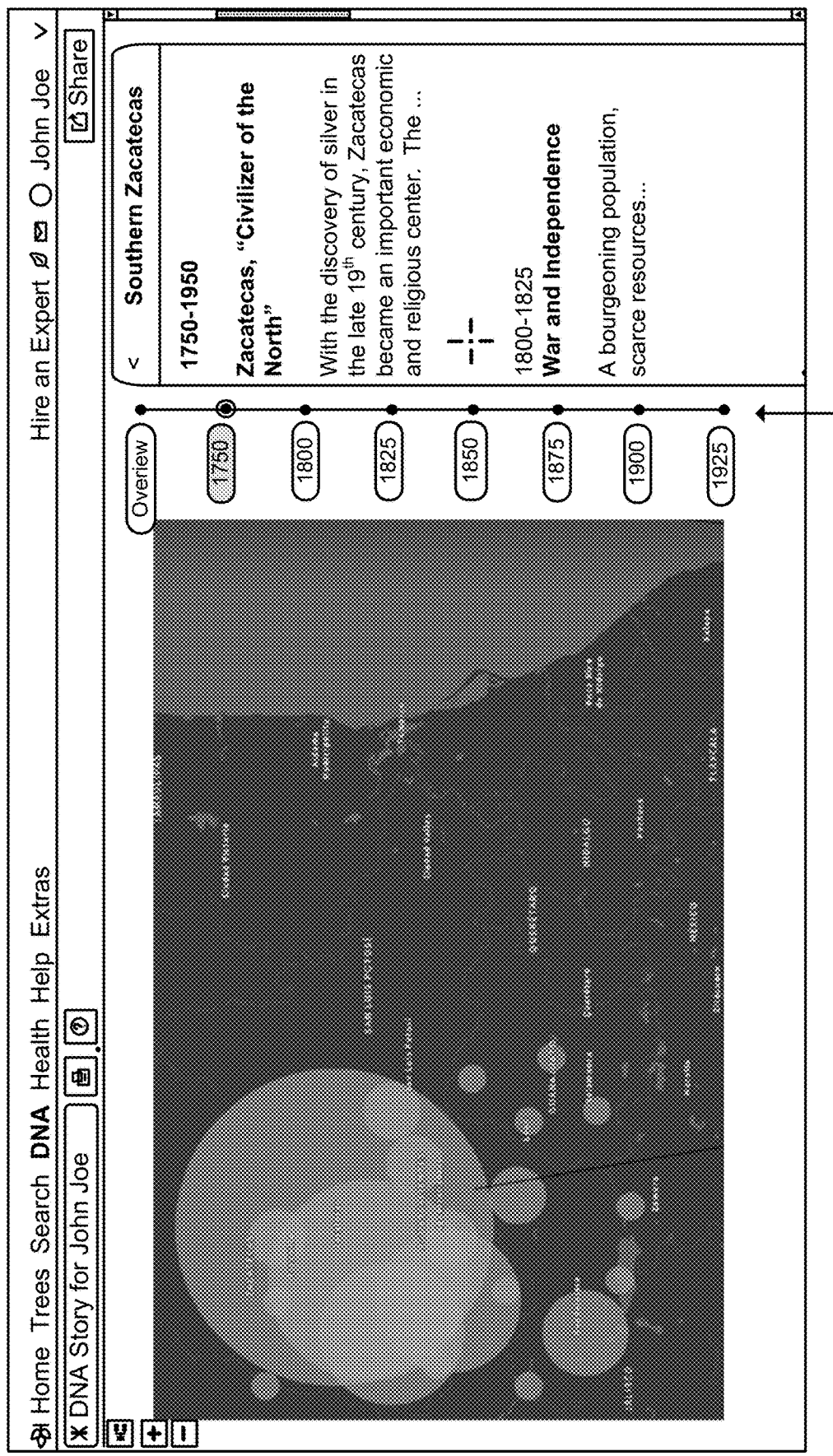
FIG. 5C shows a third view of the second mode of the storytelling interface, in accordance with some embodiments.

A user may click on the year 1750 as shown in FIG. 5C, and the map panel automatically scales to show further breakdowns of the subregions as they existed in or otherwise pertain to 1750, and the genealogy panel 410 automatically scrolls to show a written blurb and/or image about the community in 1750. The timeline feature 575 may be arranged in any suitable way, such as by named eras (e.g., Zacatecas, "Civilizer of the North", vs. War and Independence vs. the Reconstruction phase of America vs. the Depression vs. WWII America vs. Post-War America) or according to any other suitable breakdown. When the user selects or scrolls to a portion of the genealogy panel that corresponds to a specific time, said specific time on the timeline feature 575 may be highlighted or otherwise emphasized and other, e.g., adjacent, regions of the timeline feature 575 or the genealogy panel may be faded or otherwise deemphasized so as to emphasize where the user is.

Figure 6A:
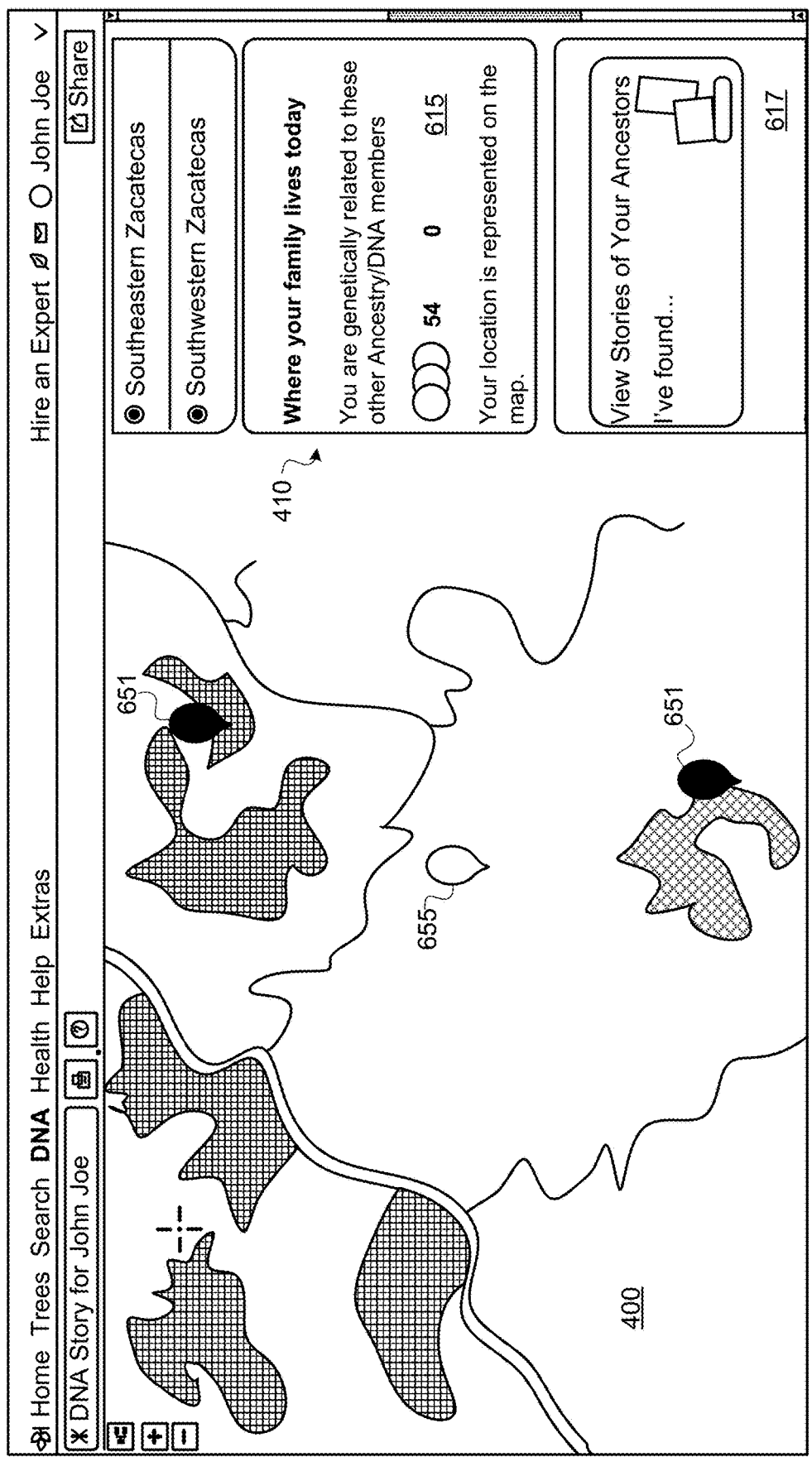
FIG. 6A shows a first view of a third mode of the storytelling interface, in accordance with some embodiments.
Figure 6B:
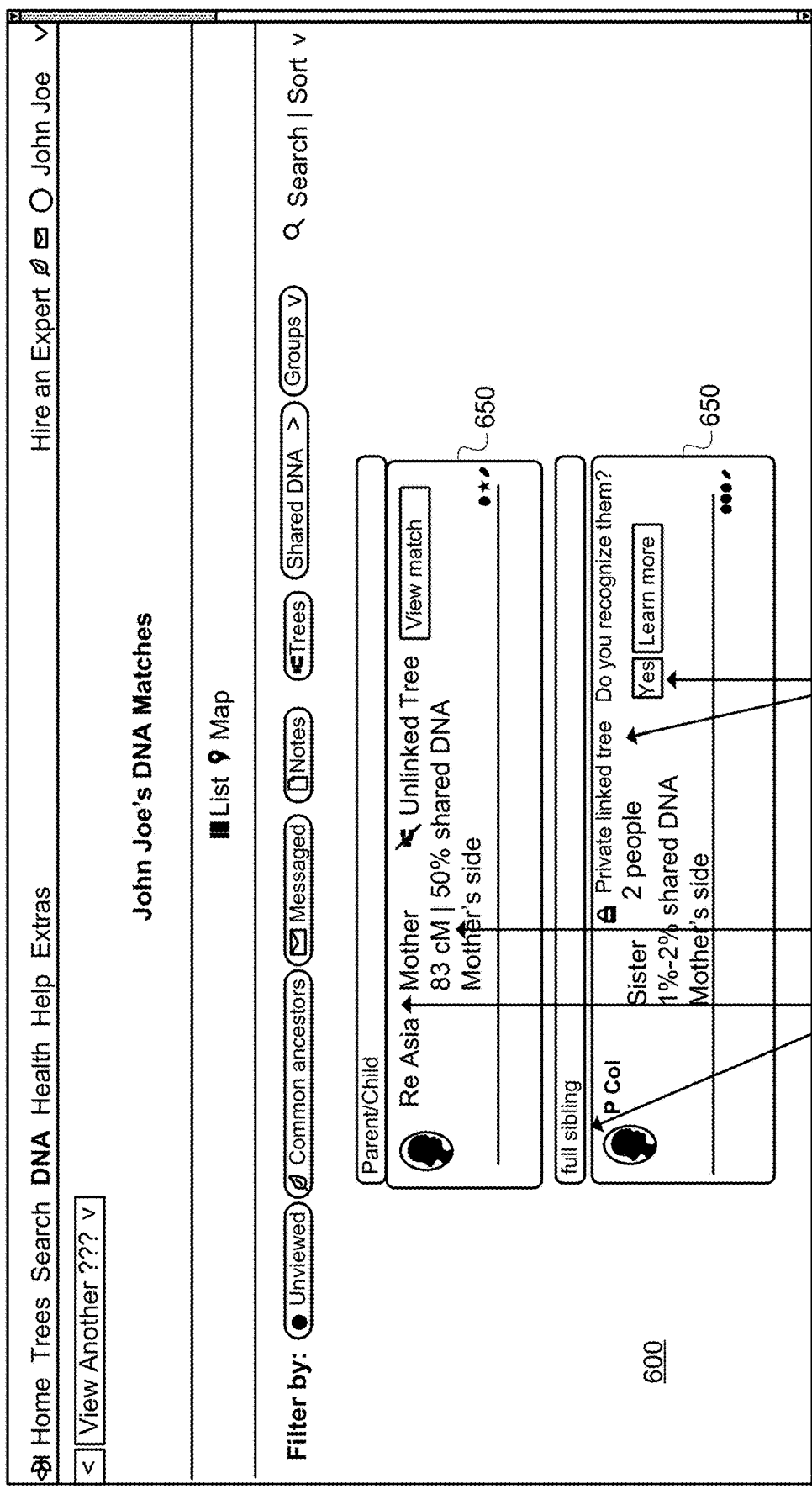
FIG. 6B shows a second view of the third mode of the storytelling interface, in accordance with some embodiments.
Figure 6C:
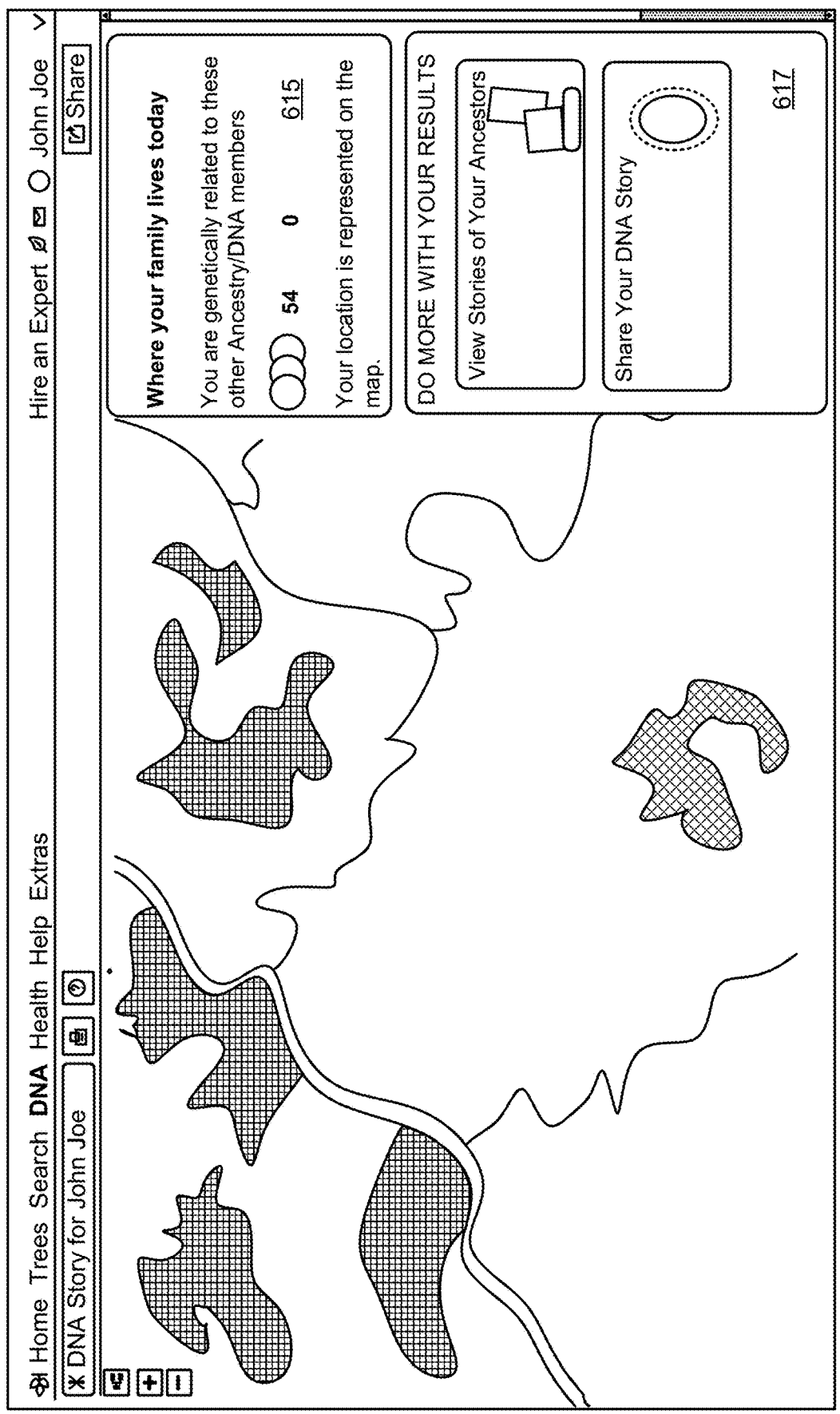
FIG. 6C shows a third view of the third mode of the storytelling interface, in accordance with some embodiments.

Turning to FIG. 6A through 6C, the user may further scroll through the genealogy panel 410 and the map panel 400 may automatically scale and relocate accordingly. The map panel 400 shows a locale specific to a genealogy segment 615 which shows a user's location 655 and nearby geography, and locations of identified relatives 651 (both the user's location and the nearby relatives are shown using icons overlaid on the map panel) as determined by the user's DNA test and/or family history information. The genealogy segment 615 shows nearby DNA matches which may be clicked on or otherwise selected and explored as shown in FIG. 6B. The map panel 400 automatically scales and locates to show the location of the user and the location of nearby matches at a scale whereat a suitable number, in some embodiments all, of the user's matches, e.g. identified relatives and communities and corresponding locations, can be simultaneously shown.

FIG. 6B shows an interface 600 of DNA matches, with individual matches 650 organized in some embodiments according to a predetermined hierarchy of relationships, with parents, siblings, avuncular, and more-distant relatives classified separately. Interface 600 may be navigated to or otherwise accessed by clicking or selecting a corresponding option in panel 410. Each match 670 shows information 680 about the relationship and degree of DNA similarity (for example number of centimorgans ("cM") and/or percentage of DNA shared and/or information/links 690 that allow a user to, for example, confirm that the detected DNA match is indeed a relative, read about the person in the site or a family tree, add the person's profile to a virtual family tree, or otherwise view or engage with the matches 650 as suitable.

Turning to FIG. 6C, the genealogy panel 410 allows for any suitable amount of additional scrolling and interaction, for example through segment 617 facilitating deeper engagement with stories of ancestors through other aspects of the site or service.

Figure 7A:
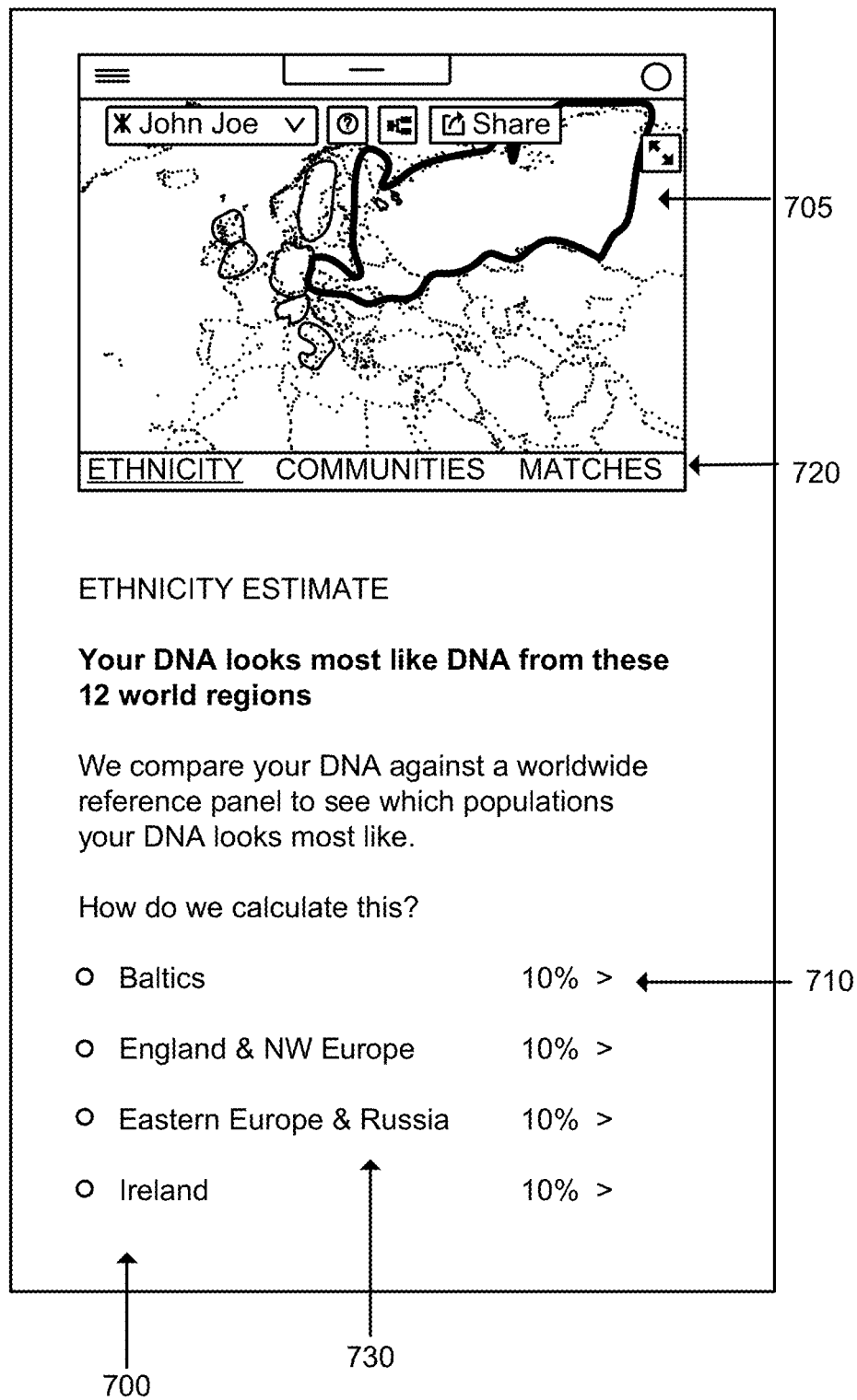
FIG. 7A shows a first view of a mobile version of the storytelling interface, in accordance with some embodiments.
Figure 7B:
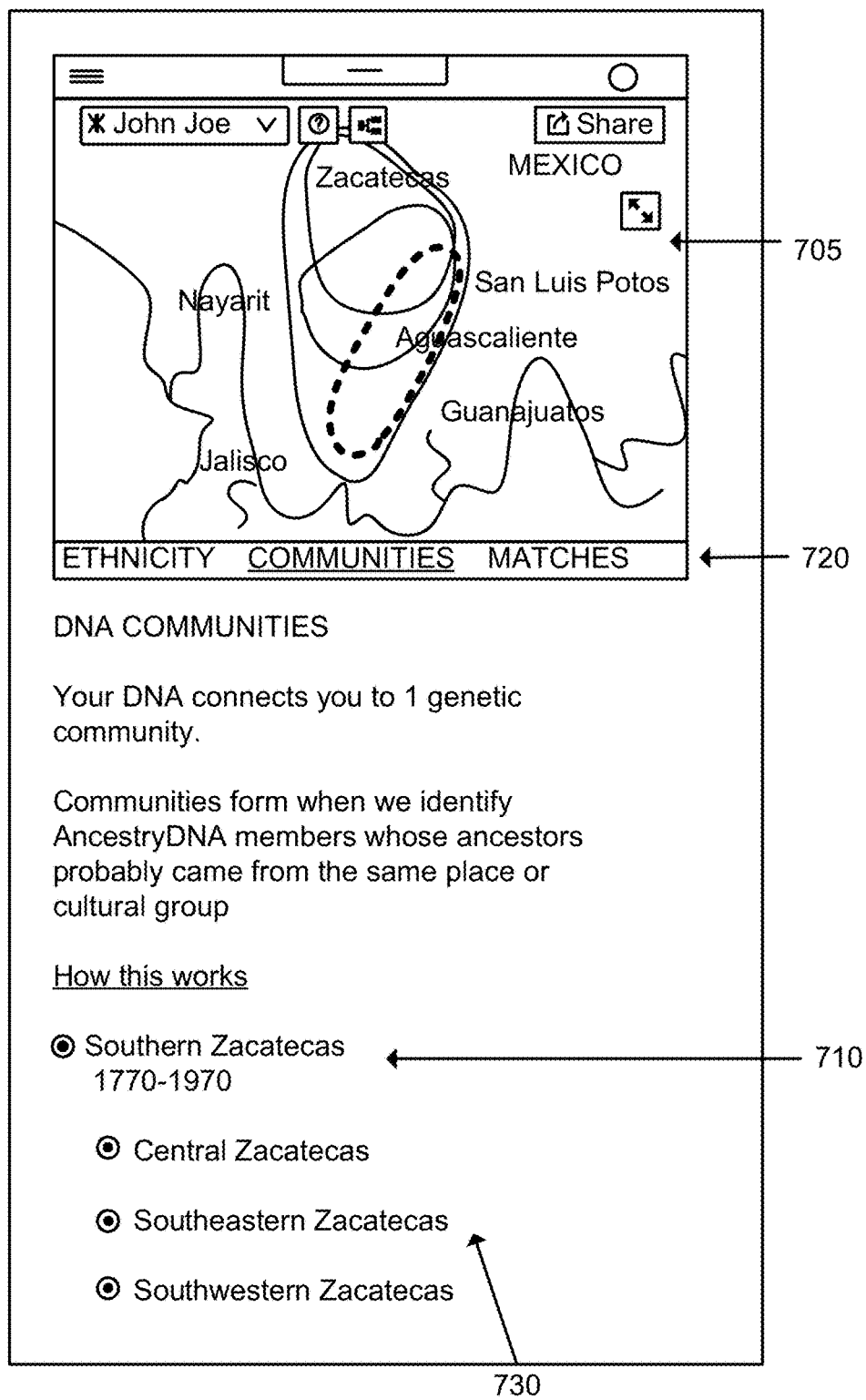
FIG. 7B shows a second view of the mobile version of the storytelling interface, in accordance with some embodiments.
Figure 7C:
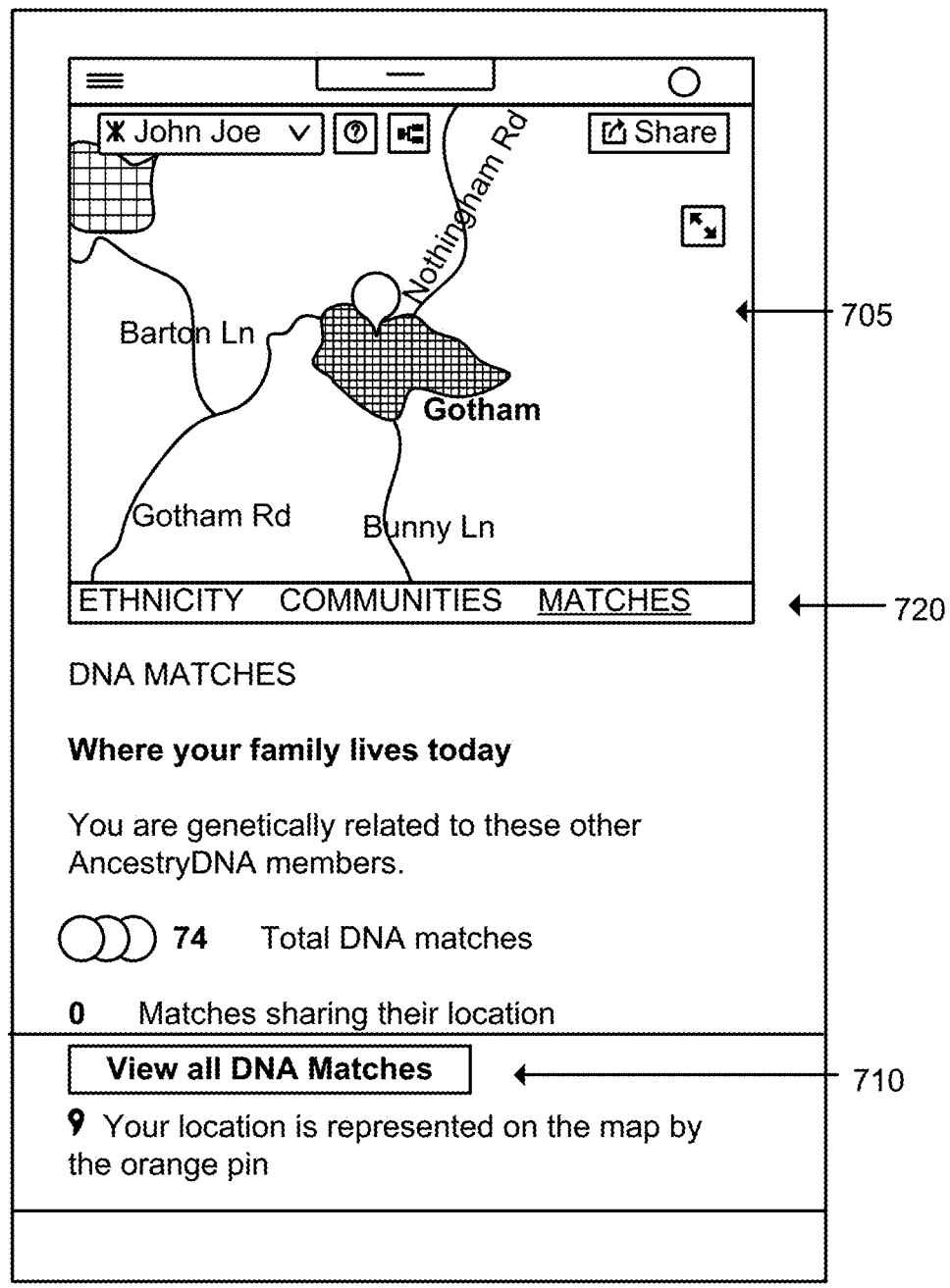
FIG. 7C shows a third view of the mobile version of the storytelling interface, in accordance with some embodiments.

Turning to FIG. 7A, FIG. 7B, and FIG. 7C, a mobile version of the storytelling interface 700 is shown and described analogous to the embodiments of FIG. 4A through FIG. 6C. The mobile version comprises a map panel 705 and a corresponding genealogy panel 710. The map panel 705 advantageously scales and locates automatically and in response to a position of the user within the genealogy panel 710. The user may scroll through the genealogy panel 710 to shift between different segments. The different segments can be provided in a tab 720. Thus, a user has the option to scroll down through the genealogy panel 710 or so to navigate directly to the desired section through the tab 720. As before, the user can hover over a segment 730 of the genealogy panel 710 to highlight a corresponding subregion or other feature of the map panel 705, or may click on the segment 730 to be navigated to a section with additional details displayed in the genealogy panel 710 regarding the selected segment 730.

While the genealogy panel of certain of the depicted embodiments has been shown on the right side of the user interface or at a top of a mobile-specific user interface, it will be appreciated that the genealogy panel is not limited to being so displayed, but rather may be displayed in any suitable location relative to the map panel. In some embodiments, rather than scrolling through the genealogy panel, the genealogy panel may be configured to allow the user to click through the features with left and right or up and down arrows, for example. Any suitable method of navigating the features may be used and is contemplated within the disclosure.

Figure 8:
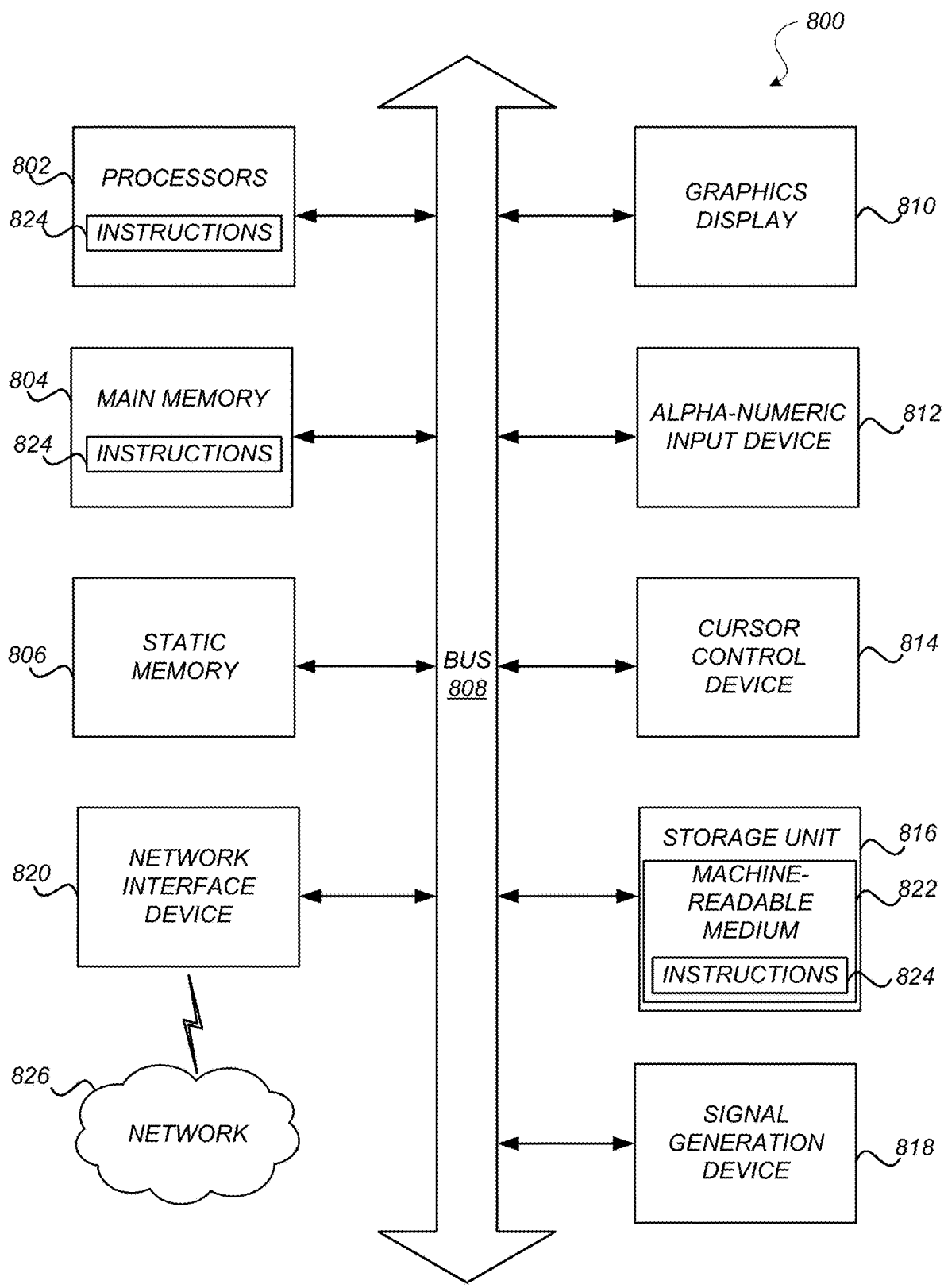
FIG. 8 is a block diagram of an example computing device, in accordance with an embodiment.

By providing a storytelling interface and associated methods according to the embodiments of the present disclosure, the problem of users being confused and/or overwhelmed by the volume and/or arrangement of information, such as DNA/ethnic community information displayed differently in time and space, is addressed. The genealogy panel facilitates continuous scrolling which simplifies the user experience without sacrificing the breadth and depth of the features and information presented to the user, while the dynamically and automatically adjustable map panel displays the corresponding map information to a user to easily and automatically visualize and interact with the pertinent information as it changes in time (by providing, e.g., a timeline feature) and space (by automatically relocating and scaling the map to a pertinent location based on the user's location in the genealogy panel). This provides a more engaging and intuitive experience for a user confronted with a challenging volume of information and features Computing Machine Architecture FIG. 8 is a block diagram illustrating components of an example computing machine that is capable of reading instructions from a computer-readable medium and execute them in a processor (or controller). A computer described herein may include a single computing machine shown in FIG. 8, a virtual machine, a distributed computing system that includes multiples nodes of computing machines shown in FIG. 8, or any other suitable arrangement of computing devices.

By way of example, FIG. 8 shows a diagrammatic representation of a computing machine in the example form of a computer system 800 within which instructions 824 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 8 may correspond to any software, hardware, or combined components shown in FIGS. 1 and 2, including but not limited to, the client device 110, the computing server 130, and various engines, interfaces, terminals, and machines shown in FIG. 2. While FIG. 8 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 824 that specify actions to be taken by that machine. Further, while only a single machine is illustrated, the term "machine" and "computer" may also be taken to include any collection of machines that individually or jointly execute instructions 824 to perform any one or more of the methodologies discussed herein.

The example computer system 800 includes one or more processors 802 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 800 may also include a memory 804 that store computer code including instructions 824 that may cause the processors 802 to perform certain actions when the instructions are executed, directly or indirectly by the processors 802. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 802 and reduces the space required for the memory 804. For example, the data illustration techniques described herein reduce the complexity of the computation of the processors 802 and data navigation of a large scale database. The algorithms described herein also reduces the size of the models and datasets to reduce the storage space requirement for memory 804.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 800 may include a main memory 804, and a static memory 806, which are configured to communicate with each other via a bus 808. The computer system 800 may further include a graphics display unit 810 (e.g., a plasma display panel (PDP), a liquid crystal display (LCD), a projector, or a cathode ray tube (CRT)). The graphics display unit 810, controlled by the processors 802, displays a graphical user interface (GUI) to display one or more results and data generated by the processes described herein. The computer system 800 may also include alpha-numeric input device 812 (e.g., a keyboard), a cursor control device 814 (e.g., a mouse, a trackball, a joystick, a motion sensor, or other pointing instrument), a storage unit 816 (a hard drive, a solid state drive, a hybrid drive, a memory disk, etc.), a signal generation device 818 (e.g., a speaker), and a network interface device 820, which also are configured to communicate via the bus 808.

The storage unit 816 includes a computer-readable medium 822 on which is stored instructions 824 embodying any one or more of the methodologies or functions described herein. The instructions 824 may also reside, completely or at least partially, within the main memory 804 or within the processor 802 (e.g., within a processor's cache memory) during execution thereof by the computer system 800, the main memory 804 and the processor 802 also constituting computer-readable media. The instructions 824 may be transmitted or received over a network 826 via the network interface device 820.

While computer-readable medium 822 is shown in an example embodiment to be a single medium, the term "computer-readable medium" should be taken to include a single medium or multiple media (e.g., a centralized or distributed database, or associated caches and servers) able to store instructions (e.g., instructions 824). The computer-readable medium may include any medium that is capable of storing instructions (e.g., instructions 824) for execution by the processors (e.g., processors 802) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. Pat. No. 10,679,729, entitled "Haplotype Phasing Models," granted on Jun. 9, 2020, (2) U.S. Pat. No. 10,223,498, entitled "Discovering Population Structure from Patterns of Identity-By-Descent," granted on Mar. 5, 2019, (3) U.S. Pat. No. 10,720,229, entitled "Reducing Error in Predicted Genetic Relationships," granted on Jul. 21, 2020, (4) U.S. Pat. No. 10,558,930, entitled "Local Genetic Ethnicity Determination System," granted on Feb. 11, 2020, (5) U.S. Pat. No. 10,114,922, entitled "Identifying Ancestral Relationships Using a Continuous Stream of Input," granted on Oct. 30, 2018, and (6) U.S. Patent Publication Application No., entitled "Linking Individual Datasets to a Database," US2021/0216556, published on Jul. 15, 2021.

What is claimed is:

1. A computer-implemented method, comprising:
causing a client device to display a graphical user interface, the graphical user interface comprising a genealogy panel occupying a first display area and a map panel occupying a second display area in the graphical user interface, the first display area being different from the second display area, the genealogy panel comprising a timeline history of an ethnic community related to a user, the genealogy panel comprising a plurality of segments, the plurality of segments comprising a first segment displaying first genealogy information related to the ethnic community, the map panel configured to display a geographical map visualizing a geographical boundary corresponding to the ethnic community responsive to the first segment being displayed;

receiving one or more actions of a user input device, wherein at least one of the actions is directed at the first display area to scroll the genealogy panel, causing the genealogy panel to continuously transition from the first segment to a second segment, the second segment displaying second genealogy information, the transition from the first segment to the second segment corresponding to a progress in the timeline history of the ethnic community; and causing, as the first display area of the genealogy panel is scrolled, the second display area of the map panel of the graphical user interface to automatically expand or contract the geographical boundary corresponding to the ethnic community as the timeline history of the ethnic community progresses.

2. The computer-implemented method of claim 1, wherein the genealogy panel is scrollable between the plurality of segments.

3. The computer-implemented method of claim 2, wherein the genealogy panel is scrollable vertically and the map panel automatically visualizes second map information corresponding to the second genealogy information responsive to a threshold portion of the second segment being scrolled into a display area of the genealogy panel.

4. The computer-implemented method of claim 1, wherein the map panel is configured to display one or more subregions corresponding to the segment of the genealogy panel that is currently displayed on the graphical user interface.

5. The computer-implemented method of claim 1, wherein the genealogy panel comprises one or more selectable options within at least one segment of the plurality of segments.

6. The computer-implemented method of claim 1, further comprising causing the map panel to highlight a subregion corresponding to a selected segment of the genealogy panel.

7. The computer-implemented method of claim 6, wherein the subregion of the map panel is the geographic boundary of the ethnic community.

8. The computer-implemented method of claim 1, further comprising causing the map panel to display only a portion of a subregion that exceeds a predetermined confidence interval threshold.

9. The computer-implemented method of claim 8, wherein the predetermined confidence interval threshold is 75%.

10. The computer-implemented method of claim 1, wherein one of the segments in the genealogy panel comprises information regarding one or more ethnic communities based on DNA results.

11. The computer-implemented method of claim 1, wherein one of the segments in the genealogy panel comprises selectable options for ethnic communities to which the user is determined to belong.

12. The computer-implemented method of claim 1, wherein the genealogy panel is configured to provide a second view when a selectable option is selected, the second view providing information pertaining to the selectable option.

13. The computer-implemented method of claim 1, wherein the map panel is capable of relocating and/or adjusting a scale continuously.

14. A system comprising:

a graphical user interface in a client device, the graphical user interface comprising a genealogy panel occupying a first display area and a map panel occupying a second display area in the graphical user interface, the first display area being different from the second display area, the genealogy panel comprising a timeline history of an ethnic community related to a user, the genealogy panel comprising a plurality of segments, the plurality of segments comprising a first segment displaying first genealogy information related to the ethnic community, the map panel configured to display a geographical map visualizing a geographical boundary corresponding to the ethnic community responsive to the first segment being displayed; and a computing server in communication with the client device, the computing server comprising a processor and memory configured to store code comprising instructions, the instructions, when executed by the processor, cause the processor to:

determine genealogy information related to a user;

transmit the genealogy information to the client device to cause the client device to display the first genealogy information related to the user in the first segment;

receive one or more actions of a user input device, wherein at least one of the actions is directed at the first display area to scroll the genealogy panel, causing the genealogy panel to continuously transition from the first segment to a second segment, the second segment displaying second genealogy information, the transition from the first segment to the second segment corresponding to a progress in the timeline history of the ethnic community; and cause, as the first display area of the genealogy panel is scrolled, the second display area of the map panel of the graphical user interface to automatically expand or contract the geographical boundary corresponding to the ethnic community as the timeline history of the ethnic community progresses.

15. The system of claim 14, wherein the genealogy panel is scrollable between the plurality of segments.

16. The system of claim 15, wherein the genealogy panel is scrollable vertically and the map panel automatically visualizes second map information corresponding to the second genealogy information responsive to a threshold portion of the second segment is scrolled into a display area of the genealogy panel.

17. The system of claim 14, wherein the map panel is configured to display one or more subregions corresponding to the segment of the genealogy panel that is currently displayed on the graphical user interface.

18. The system of claim 14, wherein the genealogy panel comprises one or more selectable options within at least one segment of the plurality of segments.

19. The system of claim 14, further comprising causing the map panel to highlight a subregion corresponding to a selected segment of the genealogy panel.

20. The system of claim 19, wherein the subregion of the map panel is the geographic boundary of the ethnic community.

\* \* \* \* \*